US012605198B2

(12) United States Patent
Cui et al.

(10) Patent No.: US 12,605,198 B2
(45) Date of Patent: Apr. 21, 2026

(54) MULTI-PATH PERFUSION CONTROL METHOD AND APPARATUS FOR INJECTION PUMP, AND INJECTION PUMP AND STORAGE MEDIUM

(71) Applicant: HANGZHOU BRONCUS MEDICAL CO., LTD., Zhejiang (CN)

(72) Inventors: Changjie Cui, Zhejiang (CN); Hong Xu, Zhejiang (CN)

(73) Assignee: Hangzhou Broncus Medical Co., Ltd., Hangzhou (CN)

( * ) Notice: Subject to any disclaimer, the term of this patent is extended or adjusted under 35 U.S.C. 154(b) by 704 days.

(21) Appl. No.: 17/957,429

(22) Filed: Sep. 30, 2022

(65) Prior Publication Data

US 2023/0025054 A1     Jan. 26, 2023

Related U.S. Application Data

(63) Continuation of application No. PCT/CN2021/072953, filed on Jan. 20, 2021.

(30) Foreign Application Priority Data

Dec. 31, 2020     (CN) ......................... 202011638325.4

(51) Int. Cl.
*A61B 18/14*          (2006.01)
*A61B 18/00*          (2006.01)

(52) U.S. Cl.
CPC .... *A61B 18/14* (2013.01); *A61B 2018/00577* (2013.01)

(58) Field of Classification Search
CPC ..... A61B 18/14; A61B 18/1492; A61B 18/12; A61B 18/1206; A61B 2018/00577;

(Continued)

(56) References Cited

U.S. PATENT DOCUMENTS 6,537,272 B2 *   3/2003   Christopherson ...... A61B 18/14
                                                                                                 606/41
6,699,243 B2 *   3/2004   West .................. A61B 18/1492
                                                                                                 606/41

(Continued)

FOREIGN PATENT DOCUMENTS

CN          1596085          3/2005
CN        202942209          5/2013

(Continued)

OTHER PUBLICATIONS

International Search Report filed in PCT/CN2021/072953 mailed Sep. 30, 2021.

*Primary Examiner* — Michael F Peffley

(57)          ABSTRACT

A multi-path perfusion control method and apparatus for injection pump, an injection pump and a storage medium, wherein the method includes: controlling the injection pump to open at least one perfusion channel when an ablation task is triggered, so as to execute a perfusion operation through an opened perfusion channel according to a preset initial flow rate; acquiring temperatures of a plurality of positions of an ablation object in real time by a plurality of temperature acquisition apparatuses; and controlling the injection pump to open or close some or all of the perfusion channels and/or adjust flow rates of some or all of the perfusion channels according to a real-time change in the temperatures of the plurality of positions. Operation delay or operation errors caused by manual determination can be reduced, and the timeliness, accuracy and pertinence of liquid perfusion during executing the ablation task can also be improved.

7 Claims, 10 Drawing Sheets

(58) Field of Classification Search
CPC ........... A61B 2018/00642; A61B 2018/00708;
A61B 2018/00744; A61B 2018/00797;
A61B 2018/00011; A61B 2018/00541;
A61B 2018/00791; A61B 2018/00982;
A61B 2018/00988; A61B 2218/002
See application file for complete search history.

(56)  References Cited

U.S. PATENT DOCUMENTS

| | | | | |
|---|---|---|---|---|
| 8,323,274 B2 * | 12/2012 | Jakus | ................. | A61B 18/1492 606/22 |
| 10,743,932 B2 * | 8/2020 | Gallardo | ............ | A61B 18/1492 |
| 2005/0171582 A1 * | 8/2005 | Matlock | ............. | A61B 18/1485 607/113 |

FOREIGN PATENT DOCUMENTS

| | | |
|---|---|---|
| CN | 104677015 | 6/2015 |
| CN | 106667650 | 5/2017 |
| CN | 109419551 | 3/2019 |
| CN | 110897710 | 3/2020 |
| WO | 9412225 | 6/1994 |
| WO | 2017085605 | 5/2017 |

* cited by examiner

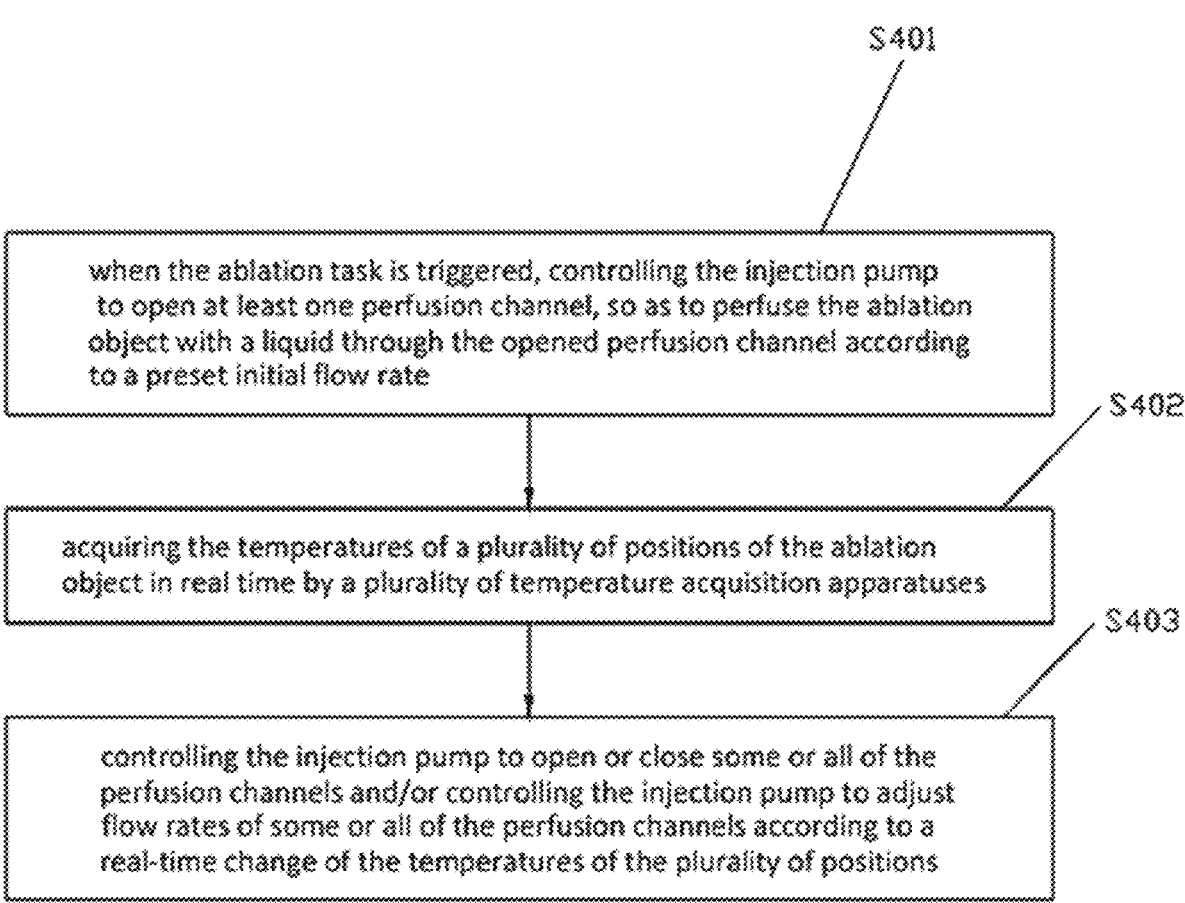

when the ablation task is triggered, controlling the injection pump to open at least one perfusion channel, so as to perfuse the ablation object with a liquid through the opened perfusion channel according to a preset initial flow rate acquiring the temperatures of a plurality of positions of the ablation object in real time by a plurality of temperature acquisition apparatuses controlling the injection pump to open or close some or all of the perfusion channels and/or controlling the injection pump to adjust flow rates of some or all of the perfusion channels according to a real-time change of the temperatures of the plurality of positions

FIG. 4

MULTI-PATH PERFUSION CONTROL METHOD AND APPARATUS FOR INJECTION PUMP, AND INJECTION PUMP AND STORAGE MEDIUM

This application claims priority of International Patent Application No. PCT/CN2021/072953, filed Jan. 20, 2021, which claims priority to Chinese Patent Application No. 202011638325.4, filed on Dec. 31, 2020, the entire contents of which are hereby incorporated by reference.

TECHNICAL FIELD

Embodiments of the present application relate to the technical field of communication, particularly to a multi-path perfusion control method and apparatus for injection pump, an injection pump and a storage medium.

BACKGROUND

Radio frequency ablation (RFA) technology is one of the most common minimally invasive tumor ablation techniques. The principle of the radio frequency ablation is to apply alternating high-frequency currents with a frequency less than 30 MHz (megahertz) to make ions in tumor tissues oscillate at high speed, rub each other, and convert radio frequency energy into heat energy, thereby causing coagulative necrosis of tumor cells.

In an ablation process, the temperature of the human body will change under the influence of the alternating high-frequency currents. Once the temperature exceeds a normal value, it will cause irreversible damage to the human body. Therefore, it is necessary to perfuse an ablation site with physiological saline in the ablation process. However, the perfusion operation of the physiological saline is generally controlled manually. When and how much liquid needs to be perfused completely depends on the treatment experience and the response ability of the doctor, and the injection pump is incapable of autonomously completing the control of the perfusion volume. As such, misjudgments and delayed operations are common.

Technical Problem

Embodiments of the present application aim to provide a multi-path perfusion control method and apparatus for injection pump, an injection pump and a storage medium, which may not only reduce operation delay and errors caused by manual determination, but also improve the timeliness, the accuracy and the pertinence of liquid perfusion during the process of executing an ablation task.

Technical Solution

In one aspect, embodiments of the present application provide a multi-path perfusion control method for injection pump, which is applied to a computer terminal and used for controlling an injection pump with a plurality of perfusion channels, the method including:

controlling the injection pump to open at least one perfusion channel when an ablation task is triggered, so as to execute a perfusion operation through an opened perfusion channel according to a preset initial flow rate;

acquiring temperatures of a plurality of positions of an ablation object in real time by a plurality of temperature acquisition apparatuses; and controlling the injection pump to open or close some or all of the perfusion channels and/or controlling the injection pump to adjust flow rates of some or all of the perfusion channels according to a real-time change in the temperatures of the plurality of positions.

In one aspect, embodiments of the present application further provide a multi-path perfusion control apparatus for injection pump, wherein the apparatus is configured for controlling an injection pump with a plurality of perfusion channels, and includes:

a control module configured for controlling the injection pump to open at least one perfusion channel when an ablation task is triggered, so as to execute a perfusion operation through the opened perfusion channel according to a preset initial flow rate; and a temperature acquisition module configured for acquiring temperatures of a plurality of positions of an ablation object in real time by a plurality of temperature acquisition apparatuses;

the control module further configured for controlling the injection pump to open or close some or all of the perfusion channels and/or controlling the injection pump to adjust flow rates of some or all of the perfusion channels according to a real-time change in the temperatures of the plurality of positions.

In one aspect, embodiments of the present application further provide an electronic apparatus, including a non-transitory memory and a processor, the non-transitory memory storing an executable program code;

the processor being electrically coupled to the non-transitory memory and a plurality of temperature acquisition apparatuses; and the processor calling the executable program code stored in the non-transitory memory to execute the multi-path perfusion control method for injection pump according to the foregoing embodiment.

In one aspect, embodiments of the present application further provide an injection pump, including a controller, a plurality of temperature acquisition apparatuses and a multi-path injection structure, the injection structure including a syringe, an extension tube, a push rod and a driving device, one end of the extension tube being connected to the syringe and the other end being provided with at least one of the temperature acquisition apparatus, and each path of the injection structure forming a perfusion channel; and the controller being electrically coupled to the plurality of temperature acquisition apparatuses and electrically connected to the multi-path injection structure, for executing steps of the multi-path perfusion control method for injection pump according to the foregoing embodiments.

In one aspect, embodiments of the present application further provide a non-transitory computer-readable storage medium on which a computer program is stored, wherein the computer program, when executed by a processor implements, implements the multi-path perfusion control method for injection pump according to the foregoing embodiments.

Beneficial Effect

In the embodiments provided in the present application, intelligent and dynamic adjustment of the multi-path perfusion for injection pump based on a real-time change in the temperatures of a plurality of different positions of the ablation object during the process of executing the ablation task is realized by means of: controlling the injection pump to open at least one perfusion channel when an ablation task is triggered, so as to execute a perfusion operation through an opened perfusion channel according to a preset initial flow rate; and then, controlling the injection pump to open or close some or all of the perfusion channels and/or controlling the injection pump to adjust the flow rates of some or all of the perfusion channels according to the temperatures of the plurality of different positions of the ablation object, which are acquired by the plurality of temperature acquisition apparatuses in real time. Since the perfusion volume of the injection pump is adjusted relatively purposefully and directionally along with the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

BRIEF DESCRIPTION OF THE DRAWINGS

In order to describe the technical solutions according to the embodiments of the present application or in the prior art more clearly, the drawings needed to be used in the embodiments or in the prior art will be described briefly below. Apparently, the drawings in the following description show some embodiments of the present application. Other drawings can be obtained by persons of ordinary skill in the art based on these drawings without creative efforts.

FIG. 4 is a flow chart of a multi-path perfusion control method for injection pump provided by an embodiment of the present application;

DESCRIPTION OF THE EMBODIMENTS

In order to make the objects, technical solutions and advantages of the embodiments of the present application clearer, the technical solutions according to the embodiments of the present application will be clearly and completely described with reference to drawings in the embodiments of the present application. Apparently, the embodiments described are merely some embodiments, but not all of the embodiments of the present application. All other embodiments obtained by ordinary persons skilled in the art based on the embodiments of the present application without creative efforts shall fall within the protection scope of the present application.

Figure 1:
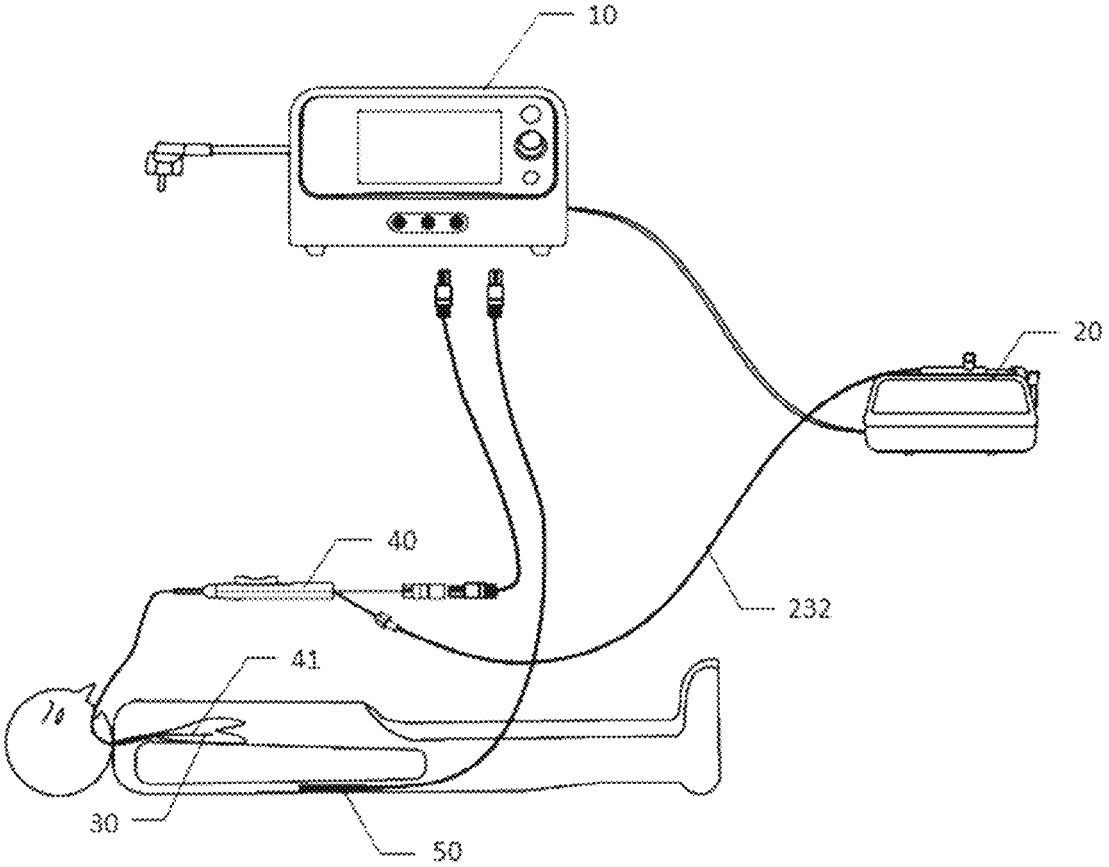
FIG. 1 is a diagram showing an application environment of a multi-path perfusion control method for injection pump provided by an embodiment of the present application.

Referring to FIG. 1, which is a schematic diagram of an application scenario of a multi-path perfusion control method for injection pump provided by an embodiment of the present application. The multi-path perfusion control method for injection pump may be implemented by a radio frequency ablation control apparatus 10 or an injection pump 20 shown in FIG. 1. Optionally, the multi-path perfusion control method for injection pump may be implemented by another computer device other than the radio frequency ablation control apparatus 10 or the injection pump 20, such as a server, a desktop computer, a notebook computer, a laptop computer, a tablet computer, a personal computer and a smart phone.

As shown in FIG. 1, a radio frequency ablation system includes the radio frequency ablation control apparatus 10, the injection pump 20 which has a plurality of perfusion channels, a plurality of temperature acquisition apparatuses 30, a radio frequency ablation catheter 40 and a neutral electrode 50. The plurality of temperature acquisition apparatuses 30 may be arranged at a top end of the radio frequency ablation catheter 40, or may be arranged at a top end of an extension tube 232 of the injection pump. The plurality of temperature acquisition apparatuses 30 are configured to acquire temperatures of a plurality of different positions of the ablation site, respectively.

Particularly, taking the radio frequency ablation control apparatus 10 as an example of an execution body of the multi-path perfusion control method for injection pump provided by the embodiment of the present application, firstly, the top end of the radio frequency ablation catheter 40 which is configured for generating and outputting radio frequency energy and the top end of the extension tube 232 of the injection pump 20 are inserted into the ablation object and reach the ablation site. Then, the neutral electrode 50 is brought into contact with the skin surface of the ablation object. The radio frequency current flows through the radio frequency ablation catheter 40, tissues of the ablation object and the neutral electrode 50, thereby forming a loop. When the ablation task is triggered, the radio frequency ablation control apparatus 10 controls the radio frequency ablation catheter 40 to output radio frequency energy to the ablation site by means of discharge, so as to execute an ablation operation on the ablation site.

Meanwhile, the radio frequency ablation control apparatus 10 controls the injection pump 20 to open at least one perfusion channel to execute the perfusion operation through the opened perfusion channel according to a preset initial flow rate, so as to perfuse the ablation site with physiological saline. Then, temperatures of a plurality of positions of the ablation site are acquired in real time by the plurality of temperature acquisition apparatuses 30. According to a real-time change in the temperatures of the plurality of positions, the injection pump 20 is controlled to open or close some or all of the perfusion channels and/or the injection pump 20 is controlled to adjust flow rates of some or all of the perfusion channels.

Figure 2:
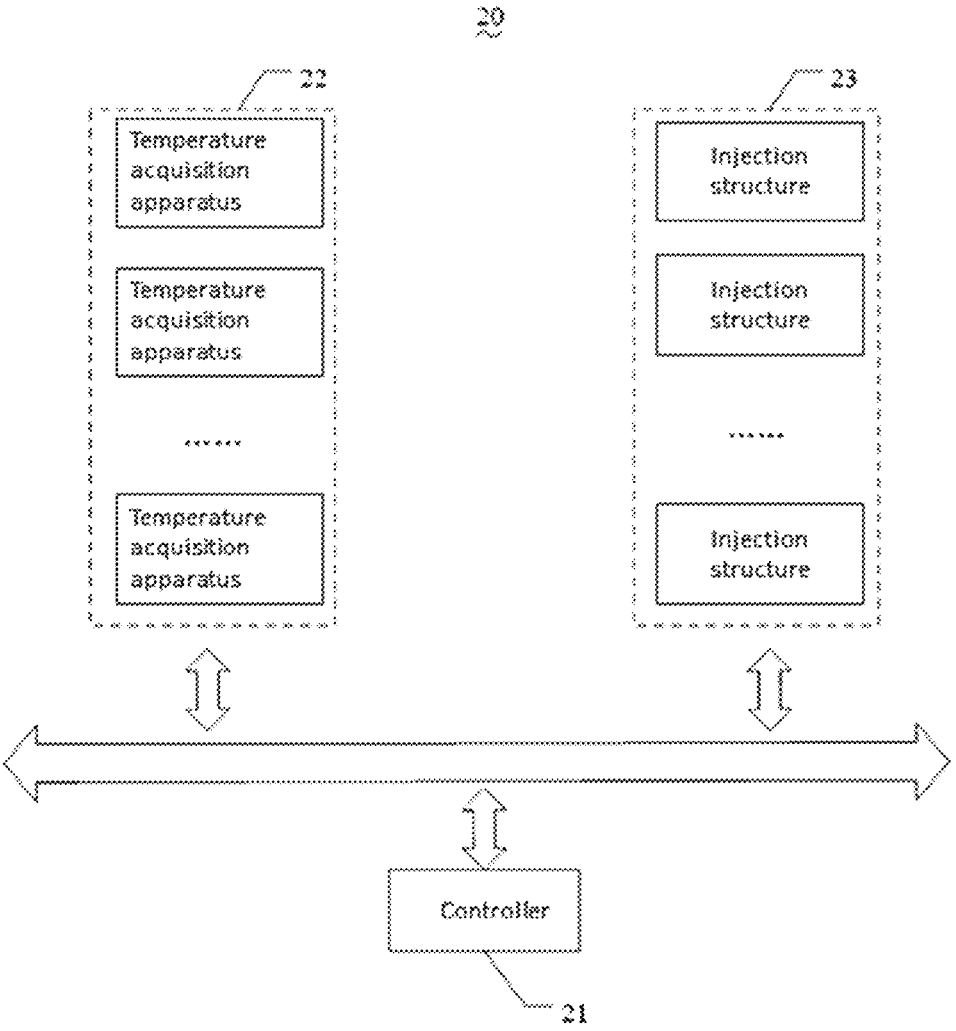
FIG. 2 is a schematic view of an internal structure of an injection pump provided by an embodiment of the present application.
Figure 3:
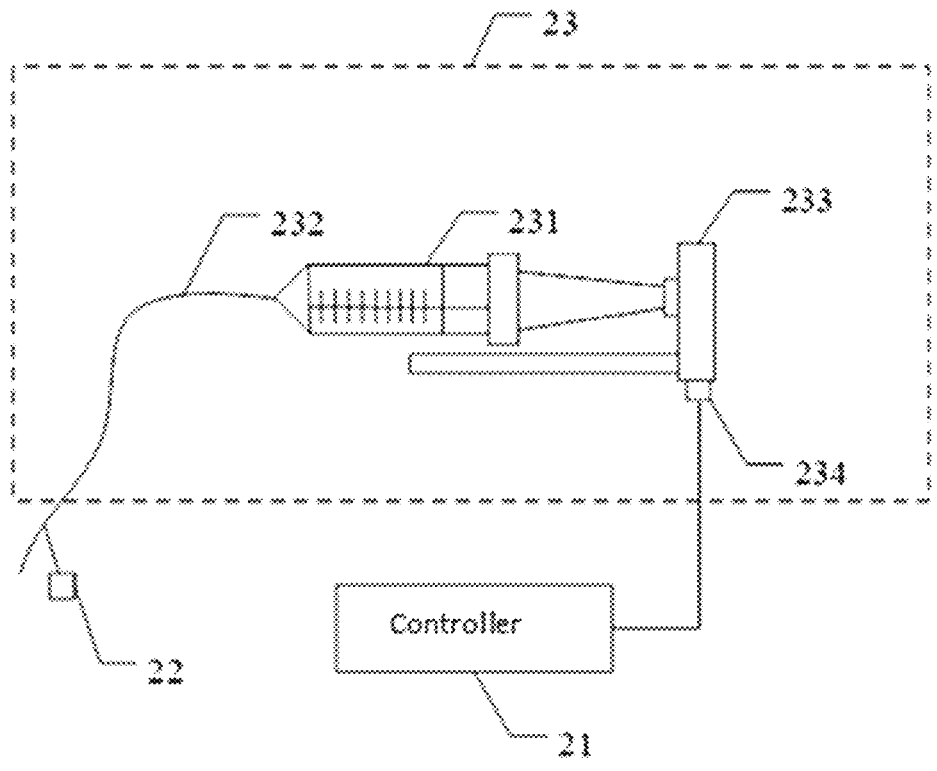
FIG. 3 is a schematic view of an internal structure of an injection structure of the injection pump as shown in FIG. 2.

Referring to FIG. 2 and FIG. 3, wherein FIG. 2 is a schematic view of an internal structure of an injection pump provided by an embodiment of the application, and FIG. 3 is a schematic view of an internal structure of an injection structure 23 shown in FIG. 2. For facilitating understanding, FIG. 2 and FIG. 3 only show structures related to the embodiment. In practical application, more or less structures may be specified than those shown in FIG. 2 and FIG. 3. As shown in FIG. 2 and FIG. 3, the injection pump 20 includes a controller 21, a plurality of temperature acquisition apparatuses 22 and a multi-path injection structure 23.

Each path of the injection structure 23 includes a syringe 231, an extension tube 232, a push rod 233 and a driving device 234. Each path of the injection structure 23 forms one perfusion channel.

One end of each extension tube 232 is connected to the syringe, and the other end is provided with at least one temperature acquisition apparatus 22 (for ease of understanding, only one is shown in the figure). One end of the push rod 233 abuts against the syringe 231, and the push rod 233 is further connected to the driving device 234 (such as a step motor).

Optionally, one end of each extension tube 232, which is provided with the temperature acquisition apparatus 22, may be fixed around a top end 41 of the radio frequency ablation catheter 40 through a fixing structure. The fixing structure is for example a catheter, a plurality of through holes are defined in a sidewall of the catheter, and a plurality of perforation holes extend through a head end and a tail end of the catheter. Each extension tube 232 and the top end 41 of the radio frequency ablation catheter 40 pass through the plurality of perforation holes, respectively. The temperature acquisition apparatus 22 disposed at one end of each extension tube 232 respectively penetrates out of the sidewall of the catheter through the nearest through hole after entering the perforation hole along with the extension tube 232. The plurality of temperature acquisition apparatuses 22 together form a claw-shaped structure for acquiring temperatures of different positions of the ablation site or ablation object.

Figure 8:
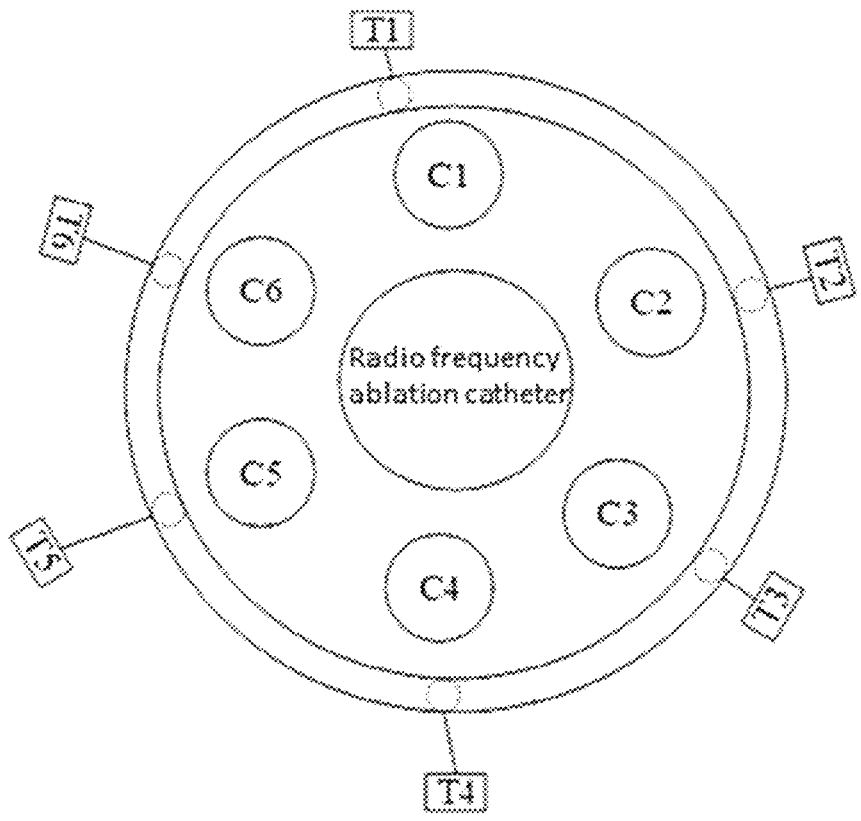
FIG. 8 is a schematic view of a layout of perfusion channels and a plurality of temperature acquisition apparatuses in the multi-path perfusion control method for injection pump provided by the embodiment of the present application.

As shown in FIG. 8, a six-path injection structure is taken as an example, a dashed circle in the figure is the through hole of the sidewall of the catheter. The six-path injection structure forms six perfusion channels, i.e., C1 to C6, which surround the radio frequency ablation catheter and correspond to six temperature acquisition apparatuses, i.e., T1 to T6, respectively. The radio frequency ablation catheter may be a unipolar radio frequency ablation catheter or a multi-polar radio frequency ablation catheter, which is not particularly limited in the present application. When the radio frequency ablation catheter is the multipolar radiofrequency ablation catheter, at least one perfusion channel may be provided around each pole of the multipolar radiofrequency ablation catheter, or one perfusion channel may be shared by a plurality of poles.

The controller 21 opens or closes the corresponding perfusion channel by controlling whether the driving apparatus 234 drives the push rod 233 to move in a designated direction. For example, when the push rod 233 pushes a tail portion of the syringe 231 forwards, the perfusion channel is opened and the liquid in the syringe 231 may flow into the ablation object along the perfusion channel. When the push rod 233 stops pushing the tail portion of the syringe 231 forwards, the perfusion channel is closed and the liquid in the syringe 231 may not flow into the ablation object along the perfusion channel any more.

In addition, the controller 21 controls the flow rate of the liquid in the perfusion channel by means of controlling a movement speed of the push rod through the driving device 234.

Optionally, a valve may be provided on the extension pipe 232 of each path of the injection structure, and the controller 21 opens or closes the corresponding perfusion channel by controlling on/off of the valve.

The controller 21 is electrically coupled to the plurality of temperature acquisition apparatuses 22 through a data line or a wireless network, and electrically connected to the multi-path injection structure 23, for executing steps of the multi-path perfusion control method for injection pump according to the embodiments shown in FIG. 4 to FIG. 7 below, for example:

when an ablation task is triggered, controlling the injection pump to open at least one perfusion channel, so as to execute a perfusion operation through the opened perfusion channel according to a preset initial flow rate;

acquiring temperatures of a plurality of positions of an ablation object in real time by a plurality of temperature acquisition apparatuses; and controlling the injection pump to open or close some or all of the perfusion channels and/or controlling the injection pump to adjust flow rates of some or all of the perfusion channels according to a real-time change in the temperatures of the plurality of positions.

A specific process of the controller 21 to implement its functions may refer to relevant descriptions in the embodiments shown in FIG. 4 to FIG. 7 below, which will be omitted here.

It should be understood that the injection pump 20 may further include other common structures such as a display screen and a power supply, which are not particularly limited in the present application.

In the embodiments of the present application, by means of the multi-path injection structure, when the ablation task is triggered, the injection pump is controlled to open at least one perfusion channel, so as to execute the perfusion operation the opened perfusion channel according to the preset initial flow rate; and then, the injection pump is controlled to open or close some or all of the perfusion channels and/or the injection pump is controlled to adjust the flow rates of some or all of the perfusion channels according to the temperatures of the plurality of different positions of the ablation object, which are acquired by the plurality of temperature acquisition apparatuses in real time. Accordingly, the multi-path perfusion of the injection pump is adjusted intelligently and dynamically based on the real-time change in the temperatures of the plurality of different positions of the ablation object during the process of executing the ablation task. Since the perfusion volume of the injection pump is adjusted relatively purposefully and directionally along with the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

Referring to FIG. 4, which is a flow chart of a multi-path perfusion control method for injection pump provided by an embodiment of the present application. The method is used to control the injection pump with a plurality of perfusion channels, such as the injection pump 20 shown in FIG. 2 and FIG. 3. The method may be implemented particularly by the injection pump 20 shown in FIG. 1, or may be implemented by the radio frequency ablation control apparatus 10 shown in FIG. 1, or may be implemented by another computer device electrically coupled to the injection pump. As shown in FIG. 4, the method particularly includes the following steps:

Step S401, when the ablation task is triggered, controlling the injection pump to open at least one perfusion channel, so as to perfuse the ablation object with a liquid through the opened perfusion channel according to a preset initial flow rate.

Particularly, the ablation task may be triggered when for example a preset trigger time is reached, a trigger instruction sent by another computer device is received, or a notification event that a user performs an operation for triggering the ablation task is detected. The operation for triggering the ablation task is for example to press a physical or virtual button for triggering the ablation task.

Optionally, after each start of the injection pump, a perfusion parameter is set to a preset initial value. The perfusion parameter may include but is not limited to an initial flow rate, a total perfusion volume, a perfusion time, and the like.

When the ablation task is triggered, the radio frequency ablation catheter starts to perform an ablation operation on the ablation object, thereby outputting radio frequency energy to the ablation object. Meanwhile, the injection pump opens at least one perfusion channel pointed by the perfusion control instruction in response to the triggered perfusion control instruction, and executes the perfusion operation through the opened perfusion channel according to the preset initial flow rate to perfuse the ablation object with a liquid, so as to adjust the temperature of the ablation object, thereby avoiding burning external tissues of the ablation object due to too high temperature or failing to achieve the ablation effect due to too low temperature.

The perfusion control command may be automatically triggered when the injection pump detects a preset event, or may be sent to the injection pump by the ablation control apparatus or another computer device electrically coupled to the injection pump. The preset event includes: the user presses a preset physical or virtual button for triggering the perfusion control instruction or an event triggers the ablation task.

Step S402, acquiring the temperatures of a plurality of positions of the ablation object in real time by a plurality of temperature acquisition apparatuses.

Particularly, the temperatures of the plurality of different positions of the ablation object are acquired in real time by the plurality of temperature acquisition apparatuses, and are used as reference data for dynamic adjustment of the perfusion volume of the injection pump.

Optionally, the temperatures of the plurality of positions of the ablation object may be acquired in real time by the following ways:

acquiring temperature sample values of the plurality of positions of the ablation object in real time by the plurality of temperature acquisition apparatuses and filtering the acquired temperature sample values;

determining whether the filtered temperature sample values exceed a preset warning value range:

when the filtered temperature sample values exceed the preset warning value range, outputting alarm information to remind the user that the operation is abnormal and whether the ablation operation needs to be stopped; and when the filtered temperature sample values do not exceed the preset warning value range, taking the minimum value or average value of the filtered temperature sample values within a preset period (for example, within 10 seconds) as the temperature for controlling the perfusion of the injection pump.

Step S403, controlling the injection pump to open or close some or all of the perfusion channels and/or controlling the injection pump to adjust flow rates of some or all of the perfusion channels according to a real-time change in the temperatures of the plurality of positions.

Particularly, the plurality of temperature acquisition apparatuses are provided in the radio frequency ablation system to acquire the temperatures of the plurality of different positions of the ablation object, respectively. The plurality of perfusion channels of the injection pump are respectively configured to perfuse the plurality of different positions of the ablation object with a liquid. After the perfusion channel is opened, the liquid automatically flows to the corresponding position via the opened perfusion channel. One perfusion channel corresponds to at least one temperature acquisition apparatus.

According to the acquired real-time temperatures of the plurality of positions, the real-time change in the temperatures of the plurality of positions is analyzed. When a real-time change trend and a change amplitude of the plurality of temperatures meet a preset adjustment condition, the injection pump is controlled to open or close some or all of the perfusion channels and/or the injection pump is controlled to adjust flow rates of some or all of the perfusion channels.

The preset adjustment condition is, for example, the acquired temperature greater than a preset maximum temperature, the acquired temperature lower than a preset minimum temperature, and the like.

The injection pump is controlled to open or close some or all of the perfusion channels and/or the injection pump is controlled to adjust the flow rates of some or all of the perfusion channels, that is, the injection pump is controlled to perform at least one of the following operations:

controlling the injection pump to open some of the perfusion channels; controlling the injection pump to close some of the perfusion channels; controlling the injection pump to open all of the perfusion channels; controlling the injection pump to close all of the perfusion channels; controlling the injection pump to adjust the flow rates of some of the perfusion channels; and controlling the injection pump to adjust flow rates of all of the perfusion channels.

The flow rate of the perfusion channel is the flow rate of the liquid in the perfusion channel. By controlling the flow rate of the liquid in the perfusion channel, the perfusion volume of the perfusion channel may be controlled, and thus the temperature of the ablation object may be regulated.

Optionally, after opening the perfusion channel, the perfusion operation may be executed automatically and directly through the opened perfusion channel at the same time.

In the embodiments of the present application, when the ablation task is triggered, the injection pump is controlled to open at least one perfusion channel through which the perfusion operation is executed according to the preset initial flow rate; and then, the injection pump is controlled to open or close some or all of the perfusion channels and/or the injection pump is controlled to adjust the flow rates of some or all of the perfusion channels according to the temperatures of the plurality of different positions of the ablation object, which are acquired by the plurality of temperature acquisition apparatuses in real time. Accordingly, the multi-path perfusion of the injection pump is adjusted intelligently and dynamically based on the real-time change in the temperatures of the plurality of different positions of the ablation object during the process of executing the ablation task. Since the perfusion volume of the injection pump is adjusted relatively purposefully and directionally according to the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

Figure 5:
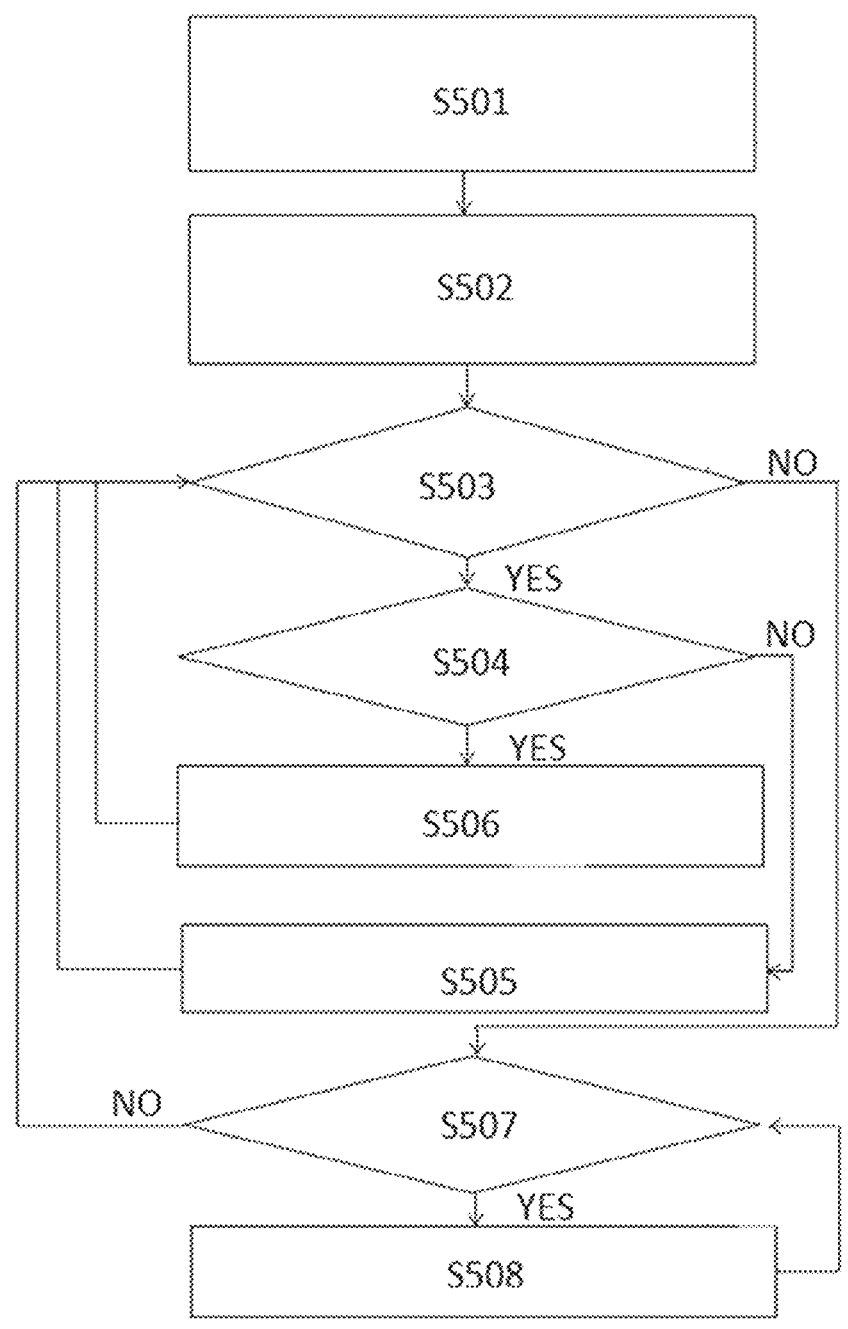
FIG. 5 is a flow chart of a multi-path perfusion control method for injection pump provided by another embodiment of the present application.

Referring to FIG. 5, which is a flow chart of a multi-path perfusion control method for injection pump provided by another embodiment of the present application. The method is used to control the injection pump with a plurality of perfusion channels, such as the injection pump 20 shown in FIG. 2 and FIG. 3. Particularly, the method may be implemented by the injection pump 20 shown in FIG. 1, or may be implemented by the radio frequency ablation control apparatus 10 shown in FIG. 1, or may be implemented by another computer device electrically coupled to the injection pump. For ease of description, the computer device is hereinafter collectively referred to as the control apparatus. As shown in FIG. 5, the method particularly includes the following steps:

Step S501, when an ablation task is triggered, controlling the injection pump to open one perfusion channel randomly, so as to perfuse the ablation object with a liquid through the opened perfusion channel according to a preset initial flow rate.

Step S502, controlling a radio frequency ablation catheter to execute an ablation operation on the ablation object, and acquiring temperatures of a plurality of positions of the ablation object in real time by a plurality of temperature acquisition apparatuses.

When the ablation task is triggered, the control apparatus firstly controls the injection pump to open one perfusion channel randomly, so as to perfuse the ablation object with the liquid through the opened perfusion channel according to the initial flow rate. Then, the radio frequency ablation catheter is controlled to perform an ablation operation on the ablation object, and meanwhile, the temperatures of the plurality of positions of the ablation object are acquired in real time by the plurality of temperature acquisition apparatuses.

In this way, the injection pump is firstly controlled to randomly open one perfusion channel before the radio frequency ablation catheter is controlled to execute the ablation operation, thereby a small amount of liquid is perfused to the ablation object through the perfusion channel, which may avoid the impact of individual specific ablation objects on other subsequent control operations using impedance values due to their high initial impedance. Moreover, perfusion of the small amount of liquid will not cause other adverse effects on the ablation object.

For unfinished details of step S501 and step S502 in this embodiment, reference may be made to related descriptions of step S401 and step S402 in the embodiment shown in FIG. 4.

Step S503, determining whether there is a first temperature in the real-time acquired temperatures of the plurality of positions.

The first temperature is greater than a preset maximum temperature. Optionally, the preset maximum temperature may be preset in an execution body of the multi-path perfusion control method for injection pump provided by the present application according to a user-defined operation.

When there is a first temperature, it performs step S504: determining whether the first perfusion channel is opened.

Particularly, when there is a first temperature in the real-time acquired temperatures of the plurality of positions, it means that the temperatures of some positions of the ablation object exceed the limit, there is a risk of damage, and the perfusion volume needs to be increased to cool these positions, thereby determining whether the first perfusion channel is opened. The first perfusion channel is configured to perfuse a first position with the liquid, and the first temperature is a temperature of the first position.

By way of example, it is assumed that four temperature acquisition apparatuses T1 to T4 are respectively configured to acquire temperatures of four positions B1 to B4 of the ablation object, and are in one-to-one correspondence to four perfusion channels C1 to C4 of the injection pump, and the preset maximum temperature is 90° C. (degrees Celsius). When the temperatures acquired by the four temperature acquisition apparatuses T1 to T4 are respectively 89.7° C., 91° C., 89.9° C. and 90.5° C., by this time, it may be known from the correspondence of the temperature acquisition apparatus, the ablation positions, the perfusion channels and the real-time acquired temperatures {(T1, B1, C1, 89.7° C.), (T2, B2, C2, 91° C.), (T3, B3, C3, 89.9° C.) and (T4, B4, C4, 90.5° C.)} and the preset maximum temperature of 90° C. that the first temperatures that exceed the limit are 91° C. and 90.5° C., the first positions that need to be cooled are B2 and B4, and the first perfusion channels that need to be regulated are C2 and C4.

Since the control apparatus controls the injection pump to randomly open one perfusion channel when the ablation task is triggered, it is necessary to determine whether the first perfusion channels C2 and C4 have been opened.

Identification information (such as serial numbers) of the plurality of perfusion channels of the injection pump is stored in the control apparatus. Moreover, each time the control apparatus controls the injection pump to open or close the perfusion channel, a corresponding log in which the identification information, the flow rate, and the opening or closing time of the perfusion channel which is controlled to be opened or closed at this time are at least recorded is generated. According to the log, the currently opened perfusion channel may be determined, such that it may be determined whether the first perfusion channels C2 and C4 have been opened.

When the first perfusion channel is not opened, it performs step S505: controlling the injection pump to open the first perfusion channel, and returning to perform step S503.

When the first perfusion channel has been opened, it performs step S506: controlling the injection pump to increase the flow rate of the first perfusion channel according to a first preset increase, and returning to perform step S503, until the flow rate of the first perfusion channel reaches a preset maximum flow rate.

Particularly, in one aspect, if the first perfusion channel is not opened, it performs the step of controlling the injection pump to open the first perfusion channel to perform the perfusion operation through all the opened first perfusion channels; and it returns to perform the step of determining whether there is a first temperature in the real-time acquired temperatures of the plurality of positions. In another aspect, if the first perfusion channel is opened, it performs the step of controlling the injection pump to increase the flow rate of the first perfusion channel according to the first preset increase, and it returns to perform the step of determining whether there is a first temperature in the real-time acquired temperatures of the plurality of positions, and so forth, until the flow rates of all the first perfusion channels reach a preset maximum flow rate.

Following the above example, if C2 of the first perfusion channels C2 and C4 has been opened but C4 has not been opened, the injection pump is controlled to open C4 and the liquid is injected into a position B4 through C4 according to the initial flow rate. Meanwhile, the injection pump is controlled to increase the flow rate of C2 according to the first preset increase to increase the perfusion volume to a position B2, so as to achieve the purpose of rapidly cooling the positons of B2 and B4.

When there is no first temperature, it performs step S507: determining whether a ratio of the first temperature acquisition apparatus in the temperature acquisition apparatuses is greater than the first ratio.

Particularly, if the first temperature greater than a preset maximum temperature does not exist in the real-time acquired temperatures of the plurality of positions, it means that the temperature of each position of the ablation object is within a safe range value, and the current ablation operation will cause no hurt to the ablation object, thereby determining whether the ratio of the first temperature acquisition apparatus in the temperature acquisition apparatuses is greater than the first ratio, so as to ensure that the ablation operation may achieve a desired ablation effect.

The temperature acquired by the first temperature acquisition apparatus within a preset duration is less than a preset minimum temperature, which is the minimum temperature limit for achieving the desired ablation effect. Optionally, the preset minimum temperature, the preset duration and the first ratio may be preset in an execution body of the multi-path perfusion control method for injection pump provided by the present application on the basis of a user-defined operation.

When the ratio is greater than the first ratio, it performs step S508: controlling the injection pump to reduce the flow rate of the second perfusion channel according to a first preset decrease, and returning to perform step S507, until the flow rate of the second perfusion channel reaches a preset minimum flow rate.

When the ratio is not greater than the first ratio, returning to perform step S503.

Particularly, in one aspect, if the ratio of the first temperature acquisition apparatus in the temperature acquisition apparatuses is greater than the first ratio, it means that the overall temperature of the ablation object is low, the increase is slow, the current perfusion volume of the liquid is too large, and the desired ablation effect may not be achieved, thereby controlling the injection pump to reduce the flow rate of the second perfusion channel according to a first preset decrease and returning to perform the step of determining whether the ratio of the first temperature acquisition apparatus in the temperature acquisition apparatuses is greater than the first ratio, and so forth, until the flow rate of the second perfusion channel reaches a preset minimum flow rate. The second perfusion channel is configured to perfuse the second position with the liquid, and the first temperature acquisition apparatus is configured to detect the temperature of the second position.

In another aspect, if the ratio of the first temperature acquisition apparatus in the temperature acquisition apparatuses is not greater than the first ratio, is means that a rate of temperature rise of the ablation object is positive, and the current perfusion volume helps the temperature rise of the ablation object, then returning to perform the step of determining whether there is a first temperature in the real-time acquired temperatures of the plurality of positions.

In this way, the perfusion volume is gradually increased or decreased according to the real-time change in the temperatures, which may improve the accuracy of perfusion control, reduce the operation risk, and achieve a better ablation effect.

Following the above example, it is assumed that a preset minimum temperature is 65° C. (degrees Celsius), the first ratio is 49%, and the preset duration is 10 seconds. When the temperatures acquired by the four temperature acquisition apparatuses T1 to T4 are 64.2° C. (for 11 seconds)), 64.3° C. (for 9 seconds), 65.1° C. (for 6 seconds) and 64.2° C. (for 12 seconds), by this time, it may be known from the correspondence of the temperature acquisition apparatuses, the ablation site, the perfusion channels and the real-time acquired temperatures {(T1, B1, C1, 64.2° C., 11s), (T2, B2, C2, 64.3° C., 9s), (T3, B3, C3, 65.1° C., 6s) and (T4, B4, C4, 64.2° C., 12s)} and the preset minimum temperature of 65° C. that the first temperature acquisition apparatuses are T1 and T4, and the ratio of the first temperature acquisition apparatus in the temperature acquisition apparatuses is 2/4=50% (greater than the first ratio of 49%), thus the second perfusion channels need to be regulated are C1 and C4. Hence, the injection pump is controlled to reduce the flow rates of C1 and C4 according to the first preset decrease, so as to reduce the perfusion volume to the positions B1 and B4, thereby achieving the effect of increasing the temperature of the positions B1 and B4.

Optionally, in another embodiment of the present application, respective preset maximum temperatures and respective preset minimum temperatures are set for each temperature acquisition apparatus, and the first perfusion channel and the second perfusion channel are determined based on the corresponding preset maximum temperatures and the preset minimum temperatures of each temperature acquisition apparatus. Then, according to the first perfusion channel and the second perfusion channel determined based on the corresponding preset maximum temperature of each temperature acquisition apparatus, it performs steps S503 to S508.

Particularly, it is determined whether there is a first temperature in the real-time acquired temperatures of the plurality of positions, wherein the first temperature is greater than a preset maximum temperature corresponding to the temperature acquisition apparatus which acquires the first temperature.

In one aspect, if there is a first temperature in the real-time acquired temperatures of the plurality of positions, determining whether the first perfusion channel is opened, wherein the first perfusion channel is configured to perfuse the first position with the liquid, and the first temperature is the temperature of the first position. If the first perfusion channel is not opened, controlling the injection pump to open the first perfusion channel, and returning to perform the step of determining whether there is a first temperature in the real-time acquired temperatures of the plurality of positions, wherein the first temperature is greater than the preset maximum temperature corresponding to the temperature acquisition apparatus which acquires the first temperature. If the first perfusion channel has been opened, controlling the injection pump to increase the flow rate of the first perfusion channel according to the first preset increase, and returning to perform the step of determining whether there is a first temperature in the real-time acquired temperatures of the plurality of positions, wherein the first temperature is greater than the preset maximum temperature corresponding to the temperature acquisition apparatus which acquires the first temperature, until the flow rate of the first perfusion channel reaches the preset maximum flow rate.

In another aspect, if there is no first temperature in the real-time acquired temperatures of the plurality of positions, determining whether the ratio of the first temperature acquisition apparatus of the temperature acquisition apparatuses is greater than the first ratio, wherein the first temperature acquisition apparatus acquires the temperature for a preset duration less than the preset minimum temperature corresponding to the first temperature acquisition apparatus. If the ratio of the first temperature acquisition apparatus is greater than the first ratio, it performs the step of controlling the injection pump to decrease the flow rate of the second perfusion channel according to the first preset decrease, and it returns to perform the step of determining whether the ratio of the first temperature acquisition apparatus of the temperature acquisition apparatuses is greater than the first ratio, until the flow rate of the second perfusion channel reaches the preset minimum flow rate, wherein the second perfusion channel is configured to perfuse the second position with the liquid, and the first temperature acquisition apparatus is configured to detect the temperature of the second position. If the ratio of the first temperature acquisition apparatus is not greater than the first ratio, it returns to perform the step of determining whether there is a first temperature in the real-time acquired temperatures of the plurality of positions, wherein the first temperature is greater than the preset maximum temperature corresponding to the temperature acquisition apparatus which acquires the first temperature.

Since there is a certain difference among the different positions of the ablation object in surface shape, internal tissue structure, and tissue thickness, the temperature changes caused by the effect of radio frequency energy are different, and temperature limits required for qualitative change are different. In this way, corresponding maximum and minimum limits are preset for the plurality of temperature acquisition apparatuses configured to acquire the temperatures of the different positions of the ablation object, which may make the perfusion control more targeted. Accordingly, the accuracy of the perfusion operation may be further improved, and thus the ablation effect is improved.

In the embodiments of the present application, intelligent and dynamic adjustment of the multi-path perfusion of the injection pump based on the real-time change in the temperatures of the plurality of different positions of the ablation object during the process of executing the ablation task is realized by means of: controlling the injection pump to open one perfusion channel through which the perfusion operation is executed according to the preset initial flow rate when the ablation task is triggered; and then, controlling the injection pump to open or close some or all of the perfusion channels and/or adjust the flow rates of some or all of the perfusion channels according to the temperatures of the plurality of different positions of the ablation object, which are acquired by the plurality of temperature acquisition apparatuses in real time. Since the perfusion volume of the injection pump is adjusted relatively purposefully and directionally along with the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

Figure 6:
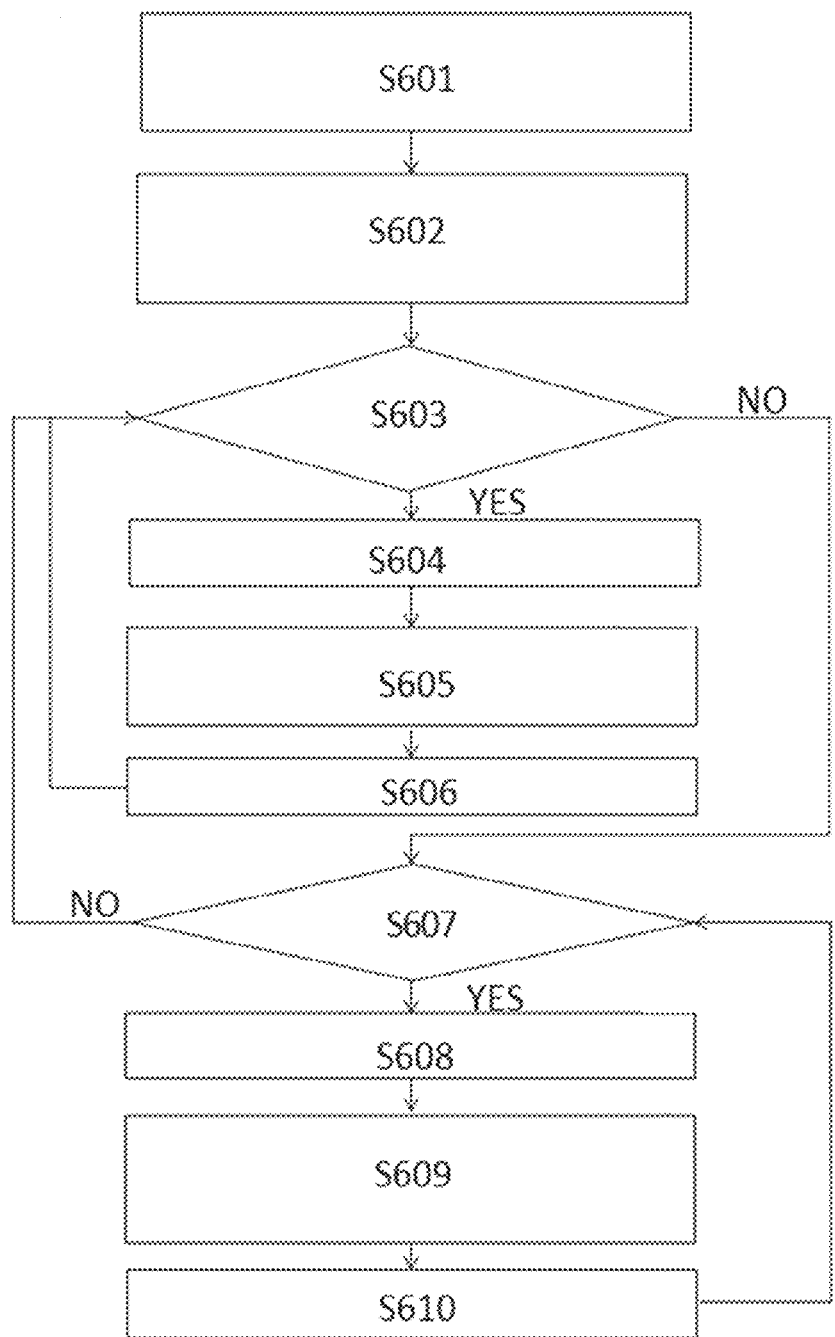
FIG. 6 is a flow chart of a multi-path perfusion control method for injection pump provided by another embodiment of the present application.

Referring to FIG. 6, which is a flow chart of a multi-path perfusion control method for injection pump according to another embodiment of the present application. The method is used to control the injection pump with a plurality of perfusion channels, such as the injection pump 20 shown in FIG. 2 and FIG. 3. The method may be implemented by the injection pump 20 shown in FIG. 1, or may be implemented by the radio frequency ablation control apparatus 10 shown in FIG. 1, or may be implemented by another computer device electrically coupled to the injection pump. For ease of description, the computer device is hereinafter collectively referred to as a control apparatus. As shown in FIG. 6, the method particularly includes the following steps:

Step S601, when an ablation task is triggered, controlling the injection pump to open one perfusion channel randomly, so as to perfuse the ablation object with a liquid through the opened perfusion channel according to a preset initial flow rate.

Step S602, controlling a radio frequency ablation catheter to perform an ablation operation on the ablation object, and acquiring temperatures of a plurality of positions of the ablation object in real time by a plurality of temperature acquisition apparatuses.

The step S601 and step S602 are the same as the step S501 and step S502 in the embodiment shown in FIG. 5. Particularly, reference may be made to related descriptions in the embodiment shown in FIG. 5, which will be omitted here.

Step S603, determining whether a ratio of the second temperature in the real-time acquired temperatures of the plurality of positions is greater than a second ratio.

The second temperature is greater than a preset maximum temperature. The second ratio may be preset in an execution body of the multi-path perfusion control method for injection pump provided by the present application on the basis of a user-defined operation.

When the ratio of the second temperature is greater than the second ratio, it performs step S604: determining a perfusion increment according to a preset increment rule.

Particularly, if the ratio of the second temperature which is greater than the preset maximum temperature of the real-time acquired temperatures of the plurality of positions is greater than the second ratio, it means that the overall temperature of the ablation object is relatively high, there is a risk of hurting these positions, and the perfusion volume needs to be increased to cool these positions, thereby determining the perfusion increment (i.e., the perfusion volume that needs to be increased) according to the preset increment rule.

The preset increment rule is: determining the perfusion increment according to the difference between the maximum temperature of the temperatures of the plurality of positions and the preset maximum temperature. The difference between the maximum temperature of the temperatures of the plurality of positions and the preset maximum temperature is in direct proportional to the perfusion increment, that is, the greater the difference is, the greater the perfusion increment required is.

Optionally, the perfusion increment and the perfusion decrement below also may be fixed values which are preset in the control apparatus according to the user-defined operation.

Particularly, the correspondence between a plurality of difference intervals and the preset perfusion increments may be preset in the control apparatus. Firstly, it is determined that which difference interval the maximum temperature of the temperatures of the plurality of positions falls into, and then the preset perfusion increment corresponding to the fell difference interval is determined as the required perfusion increment according to the fell difference interval and the above preset correspondence.

Step S605, determining the opening number according to the perfusion increment and the initial flow rate, and determining the third perfusion channel according to the opening number and a first determination rule.

It should be understood that the initial flow rate of each perfusion channel is the same. At the beginning of each time the injection pump controls the opening of the perfusion channel, it will perform the perfusion operation through the opened perfusion channel according to the initial flow rate.

Particularly, the first determination rule is: determining the third perfusion channel from near to far according to a distance from the second temperature acquisition apparatus and the opening number, wherein a temperature acquired by the second temperature acquisition apparatus is maximum. Further, if there are several perfusion channels with the same distance from the second temperature acquisition apparatus, the required third perfusion channel is randomly determined from them.

According to the perfusion increment and the initial flow rate, a calculation formula for determining the opening number is for example described as follows: the value obtained by dividing the perfusion increment by the initial flow rate is rounded and then added with one.

For example, with reference to FIG. 8, it is assumed that 6 temperature acquisition apparatuses T1 to T6 correspond to 6 positions B1 to B6 of the ablation object, and the 6 perfusion channels C1 to C6 of the injection pump are configured to perfuse B1 to B6 with the liquid, respectively. If the preset maximum temperature is 90° C., the second ratio is 50%, and the acquired temperatures of the positions B1 to B6 in real time from T1 to T6 are 90.2° C., 80.9° C., 90.1° C., 90.3° C., 80.8° C. and 90.3° C., respectively, there are four second temperatures, which are 90.2° C., 90.1° C., 90.3° C. and 90.3° C., respectively. It may be seen that the ratio of the second temperature of all acquired temperatures of the six temperature acquisition apparatuses T1 to T6 is 4/6≈67%, which is greater than the second ratio of 50%. Hence, according to the difference of 0.3° C. between the maximum temperature of 90.3° C. of the six temperatures and the preset maximum temperature of 90° C. and the correspondence between the plurality of preset difference intervals and the preset perfusion increment, the required perfusion increment is determined, which is assumed to be 0.5 ml. Then, according to the initial flow rate of each perfusion channel (assumed to be 0.2 ml) and the determined perfusion increment, the opening number is determined to be [(0.5/0.2)]+1=3. Finally, the third perfusion channels to be opened from near to far are determined to be C5, C1 and C2, respectively according to the distance from the second temperature acquisition apparatus T6 (acquiring the maximum temperature) and the opening number.

Step S606, controlling the injection pump to open the third perfusion channel, and returning to perform step S603, until all the perfusion channels are opened.

Identification information of the plurality of perfusion channels of the injection pump is stored in the control apparatus. The injection pump is controlled to open the third perfusion channel according to the identification information, and returns to perform the step of determining whether the ratio of the second temperature of the real-time acquired temperatures of the plurality of positions is greater than the second ratio, until all the perfusion channels are opened.

Further, every time the control apparatus controls the injection pump to open or close the perfusion channel, a corresponding log in which the identification information, the flow rate, and the opening or closing time of the perfusion channel controlled to be opened or closed at this time is at least recorded is generated. Before the injection pump is controlled to open the third perfusion channel, whether the third perfusion channel has been opened may be determined according to the log, if not been opened, the third perfusion channel is opened; if been opened, the third perfusion channel is skipped and a perfusion channel adjacent to the third perfusion channel is opened. Following the above example, if C2 has been opened, opening the perfusion channel C3 adjacent to the C2. It should be understood that if the C3 has been opened, opening the perfusion channel C4 sequentially, and so forth, until all the perfusion channels are opened or the number of the opened third perfusion channels reaches the number of the perfusion channels to be opened.

Further, after all the perfusion channels are opened, if the ratio of the second temperature is still greater than the second ratio, it means that the previous perfusion adjustment effect is poor, and the overall temperature of the ablation object is still too high, thereby controlling the injection pump to increase the flow rate of all the perfusion channels from the initial flow rate to a preset maximum flow rate at one time, so as to achieve a rapid cooling effect.

When the ratio of the second temperature is not greater than the second ratio, it performs step S607: determining whether the ratio of the third temperature acquisition apparatus of the temperature acquisition apparatuses is greater than a third ratio.

Particularly, if the ratio of the second temperature greater than the preset maximum temperature of the real-time acquired temperatures of the plurality of positions is not greater than the second ratio, it means that the overall temperature of the ablation object is within a safe value range, and the current ablation operation will cause no hurt to the ablation object, thereby determining whether the ratio of the third temperature acquisition apparatus of the temperature acquisition apparatuses is greater than the third ratio, so as to ensure that the ablation operation may achieve the desired ablation effect. The temperature acquired by the third temperature acquisition apparatus is less than a preset minimum temperature. The third ratio may be preset in an execution body of the multi-path perfusion control method for injection pump provided by the present application on the basis of a user-defined operation.

If the ratio of the third temperature acquisition apparatus is greater than the third ratio, it performs step S608: determining a perfusion decrement according to a preset decrement rule.

If the ratio of the third temperature acquisition apparatus of all the temperature acquisition apparatuses is greater than the third ratio, it means that the overall temperature of the ablation object is slightly low, the current perfusion volume of the liquid is too large, and the desired ablation effect may not be achieved, thereby determining the perfusion decrement according to the preset decrement rule.

The preset decrement rule is: determining the perfusion decrement according to the difference between the minimum temperature of the temperatures of the plurality of positions and the preset minimum temperature. The difference between the minimum temperature and the preset minimum temperature is in direct proportional to the perfusion decrement, that is, the greater the difference is, the greater the perfusion decrement required is.

Particularly, the correspondence between the plurality of difference intervals and the preset perfusion decrement may be preset in the control apparatus. Firstly, it is determined that which difference interval the minimum temperature of the temperatures of the plurality of positions falls into, and then the perfusion decrement corresponding to the fell difference interval is determined as the required perfusion decrement according to the fell difference interval and the preset correspondence.

Step S609, determining the closing number according to the perfusion decrement and the initial flow rate, and determining the fourth perfusion channel according to the closing number and a second determination rule.

Particularly, according to the perfusion decrement and the initial flow rate, a calculation formula for determining the closing number is for example described as follows: the value obtained by dividing the perfusion decrement by the initial flow rate is rounded and then added with one.

The second determination rule is: determining the fourth perfusion channel from near to far according to a distance from the fourth temperature acquisition apparatus and the closing number, wherein the fourth temperature acquisition apparatus acquires the minimum temperature.

A method for determining the fourth perfusion channel is similar to that for determining the third perfusion channel. Particularly, reference may be made to related descriptions in the S605, which will be omitted here.

Step S610, controlling the injection pump to close the fourth perfusion channel, and returning to step S607, until all the perfusion channels are closed.

According to the identification information of each perfusion channel, the control apparatus controls the injection pump to close the fourth perfusion channel, and return to perform the step of determining whether the ratio of the third temperature acquisition apparatus of the temperature acquisition apparatuses is greater than the third ratio, until all the perfusion channels are closed.

Further, if the fourth perfusion channel to be closed has been closed, a perfusion channel adjacent to the fourth perfusion channel is closed. If the adjacent perfusion channel is closed, the next perfusion channel adjacent to the adjacent perfusion channel is sequentially closed, and so forth, until all the perfusion channels are closed, or the number of the closed fourth perfusion channels reaches the closing number.

If the ratio of the third temperature acquisition apparatus of all the temperature acquisition apparatuses is not greater than the third ratio, it returns to preform step S603: determining whether the ratio of the second temperature of the real-time acquired temperatures of the plurality of positions is greater than the second ratio.

In this way, the perfusion volume is gradually increased or decreased according to the real-time change in the temperatures, which may improve the accuracy of perfusion control, reduce the operation risk, and achieve a better ablation effect.

For unfinished details in this embodiment, reference may be made to related contents in the embodiments shown in FIG. 4 and FIG. 5.

In the embodiments of the present application, when the ablation task is triggered, the injection pump is controlled to open at least one perfusion channel through which the perfusion operation is executed according to the preset initial flow rate; and then, the injection pump is controlled to open or close some or all of the perfusion channels and/or adjust the flow rates of some or all of the perfusion channels according to the temperatures of the plurality of different positions of the ablation object, which are acquired by the plurality of temperature acquisition apparatuses in real time. Accordingly, the multi-path perfusion of the injection pump is adjusted intelligently and dynamically based on the real-time change in the temperatures of the plurality of different positions of the ablation object during the process of executing the ablation task. Since the perfusion volume of the injection pump is adjusted relatively purposefully and directionally along with the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

Figure 7:
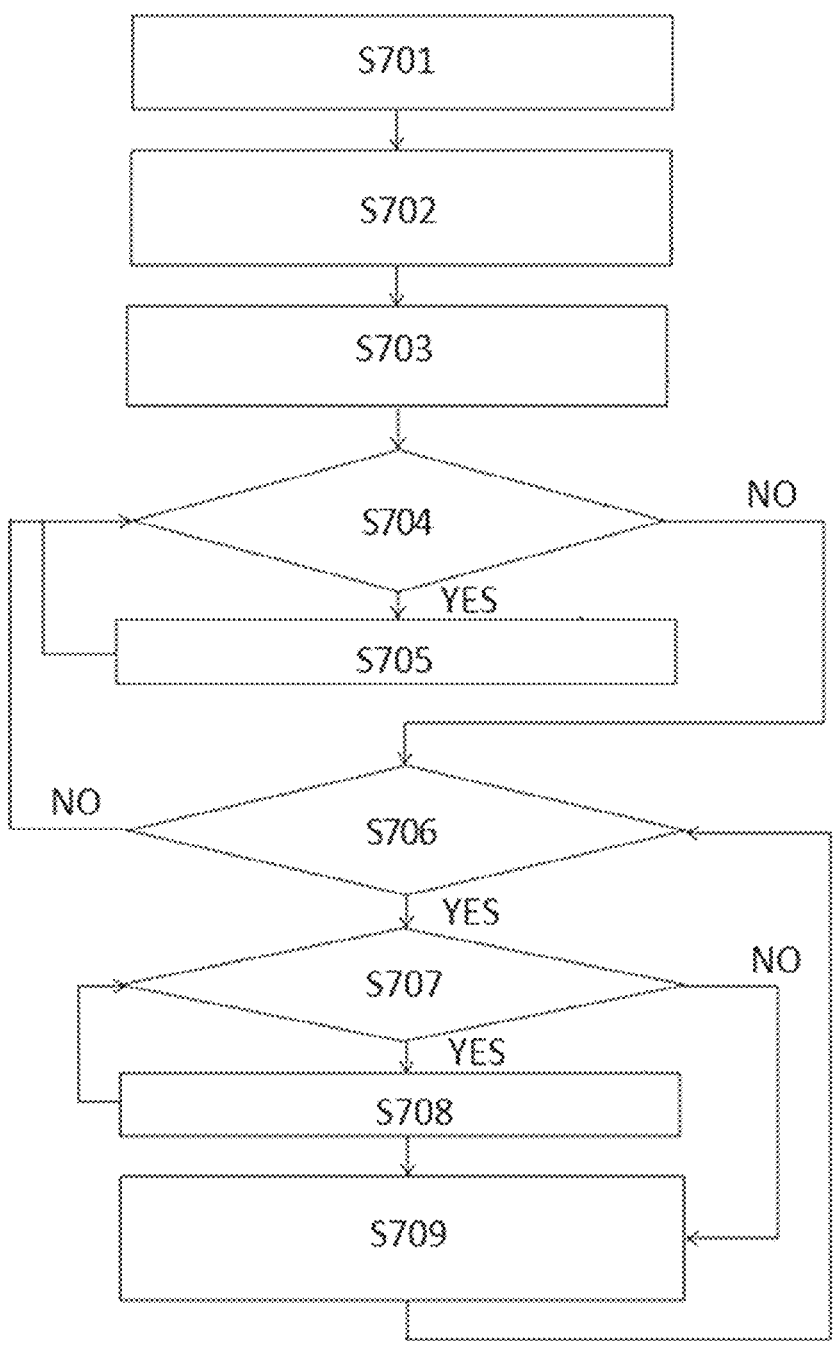
FIG. 7 is a flow chart of a multi-path perfusion control method for injection pump provided by another embodiment of the present application.

Referring to FIG. 7, which is a flowchart of a multi-path perfusion control method for injection pump provided by another embodiment of the present application. The method is used to control the injection pump with a plurality of perfusion channels, such as the injection pump 20 shown in FIG. 2 and FIG. 3. The method may be implemented by the injection pump 20 shown in FIG. 1, or may be implemented by the radio frequency ablation control apparatus 10 shown in FIG. 1, or may be implemented by another computer device electrically coupled to the injection pump. For ease of description, the computer device is hereinafter collectively referred to as a control apparatus. As shown in FIG. 7, the method particularly includes the following steps.

Step S701, when the ablation task is triggered, controlling a radio frequency ablation catheter to perform an ablation operation.

Particularly, the ablation task may be triggered when for example a preset trigger time is reached, a trigger instruction sent by another control apparatus is received, or a notification event that a user performs an operation for triggering the ablation task is detected. The operation for triggering the ablation task is for example to press a physical or virtual button for triggering the ablation task.

Optionally, after each start of the injection pump, a perfusion parameter is set to a preset initial value. The perfusion parameter may include but is not limited to an initial flow rate, a total perfusion volume, a perfusion time, and the like.

When the ablation task is triggered, the radio frequency ablation catheter is controlled to start performing an ablation operation on the ablation object, so as to output radio frequency energy to the ablation object.

Step S702, controlling the injection pump to open all perfusion channels after waiting for a preset duration, so as to perfuse the ablation object with a liquid through the opened perfusion channel according to the initial flow rate.

Particularly, the preset duration may be preset in an execution body of the multi-path perfusion control method for injection pump provided by the present application on the basis of a user-defined operation.

It should be understood that in order to achieve the desired ablation effect, the temperature of the ablation object needs to reach a certain degree. After the radio frequency ablation catheter is controlled to perform the ablation operation and waits for the preset duration, the temperature of the ablation object rises to a certain degree, and then the injection pump is controlled to open all perfusion channels to perform the perfusion operation, which may prevent premature perfusion from influencing the rate of the temperature rise of the ablation object and ensure a better ablation effect.

Step S703, acquiring the temperatures of plurality of positions of the ablation object in real time by a plurality of temperature acquisition apparatuses.

Particularly, step S703 may refer to related descriptions of step S402 in the embodiment shown in FIG. 4, which will be omitted here.

Step S704, determining whether a ratio of a third temperature of the real-time acquired temperatures of the plurality of positions is greater than a fourth ratio.

If the ratio of the third temperature is greater than the fourth ratio, it performs step S705: closing one opened perfusion channel randomly, and returning to perform step S704.

Particularly, the third temperature is less than a preset minimum temperature. If the ratio of the third temperature less than the preset minimum temperature of the real-time acquired temperatures of the plurality of positions is greater than a fourth ratio, it means that the current perfusion volume is too large, and the overall temperature of the ablation object is unsatisfied, thereby closing one opened perfusion channel randomly to decrease the perfusion volume, and returning to perform the step of determining whether the ratio of the third temperature of the real-time acquired temperatures of the plurality of positions is greater than the fourth ratio, until all the perfusion channels are closed.

If the ratio of the third temperature is not greater than the fourth ratio, it performs step S706: determining whether the ratio of the fourth temperature of the real-time acquired temperatures of the plurality of positions is greater than a fifth ratio.

When the ratio of the fourth temperature is greater than the fifth ratio, it performs step S707: determining whether there is an unopened perfusion channel.

When there is an unopened perfusion channel, it performs step S708: opening one unopened perfusion channel randomly, and returning to perform step S706, until all the perfusion channels are opened.

When there is not unopened perfusion channel, it performs step S709: increasing the flow rate of each perfusion channel according to a preset second increase, and returning to perform step S706, until the flow rate of each perfusion channel reaches a preset maximum flow rate.

When the ratio of the fourth temperature is not greater than the fifth ratio, it returns to perform step S704.

Particularly, if the ratio of the third temperature less than the preset minimum temperature of the real-time acquired temperatures of the plurality of positions is not greater than the fourth ratio, it means that the overall temperature of the ablation object reaches the desired temperature, and the current perfusion volume is helpful for the temperature rise of the ablation object, thereby determining whether the ratio of the fourth temperature of the real-time acquired temperatures of the plurality of positions is greater than the fifth ratio for prevent the ablation object from being hurt by excess temperature. The fourth temperature is greater than a preset maximum temperature. The fourth ratio and the fifth ratio may be preset in an execution body of the multi-path perfusion control method for injection pump provided by the present application on the basis of a user-defined operation.

In one aspect, if the ratio of the fourth temperature of the real-time acquired temperatures of the plurality of positions is greater than the fifth ratio, it means that the overall temperature of the ablation object is too high, these positions may be hurt, and the perfusion volume needs to be increased to cool these positions, thereby determining whether there is an unopened perfusion channel. If there is an unopened perfusion channel, one unopened perfusion channel is randomly opened, and it returns to perform the step of determining whether the ratio of the fourth temperature of the real-time acquired temperatures of the plurality of positions is greater than the fifth ratio, until all the perfusion channels are opened. If all the perfusion channels are opened, the flow rate of the perfusion channel is increased according to the second preset increase, and it returns to perform the step of determining whether the ratio of the fourth temperature of the real-time acquired temperatures of the plurality of positions is greater than the fifth ratio, until the flow rate of the perfusion channel reaches the preset maximum flow rate. Furthermore, if the ratio of the fourth temperature of the real-time acquired temperatures of the plurality of positions after the flow rate of the perfusion channel reaches the preset maximum flow rate is still greater than the fifth ratio, alarm information is output.

In another aspect, if the ratio of the fourth temperature of the real-time acquired temperatures of the plurality of positions is not greater than the fifth ratio, it returns to perform the step of determining whether the ratio of the third temperature of the real-time acquired temperatures of the plurality of positions is greater than the fourth ratio.

In this way, according to the real-time change in the temperatures, the perfusion volume is gradually increased or decreased by increasing or decreasing the number of the perfusion channels, which may improve the accuracy of the perfusion control, reduce the operation risk and achieve a better ablation effect.

For unfinished details in this embodiment, reference may further be made to related descriptions in the embodiments shown in FIG. 4 to FIG. 6.

In the embodiments of the present application, when the ablation task is triggered, the radio frequency ablation catheter is firstly controlled to perform the ablation operation; the injection pump is controlled to open all perfusion channels after waiting for a preset duration, so as to perfuse the ablation object with the liquid through the opened perfusion channels according to the initial flow rate; and then the injection pump is controlled to open or close some or all of the perfusion channels and/or adjust the flow rates of some or all of the perfusion channels according to the temperatures of the plurality of different positions of the ablation object, which are acquired by the plurality of temperature acquisition apparatuses in real time. Accordingly, the multi-path perfusion of the injection pump is adjusted intelligently and dynamically based on the real-time change in the temperatures of the plurality of different positions of the ablation object during the process of executing the ablation task. Since the perfusion volume of the injection pump is adjusted relatively purposefully and directionally along with the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

Figure 9:
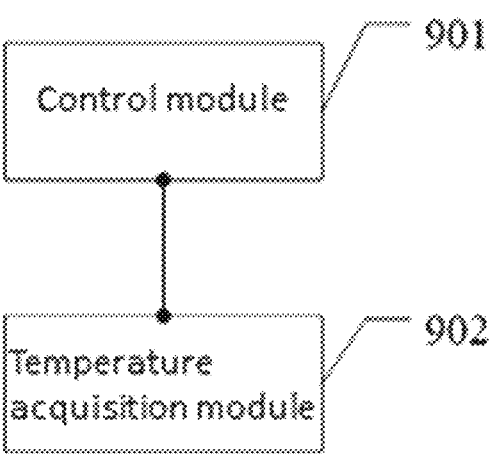
FIG. 9 is a schematic view of an multi-path perfusion control apparatus for injection pump provided by an embodiment of the present application.

Referring to FIG. 9, which is a schematic view of a multi-path perfusion control apparatus for injection pump provided by an embodiment of the present application. For ease of description, only parts related to embodiments of the present application are shown. The apparatus may be an injection pump 20, a radio frequency ablation control apparatus 10 shown in FIG. 1 or other computer terminals, or may be a virtual module running in the foregoing apparatus. The apparatus is configured to control the injection pump with a plurality of perfusion channels, and particularly includes a control module 901 and a temperature acquisition module 902.

The control module 901 is configured to control the injection pump to open at least one perfusion channel when an ablation task is triggered, so as to perform a perfusion operation through the opened perfusion channel according to a preset initial flow rate.

The temperature acquisition module 902 is configured to acquire temperatures of plurality of positions of an ablation object in real time by a plurality of temperature acquisition apparatuses.

The control module 901 is further configured to control the injection pump to open or close some or all of the perfusion channels and/or control the injection pump to adjust flow rates of some or all of the perfusion channels according to the real-time change in the temperatures of the plurality of positions.

Optionally, the control module 901 includes:

a first control submodule, which is configured to control the injection pump to open one perfusion channel when the ablation task is triggered, so as to perfuse the ablation object with a liquid through the opened perfusion channel according to the preset initial flow rate; and the first control submodule is further configured to control a radio frequency ablation catheter to perform the ablation operation on the ablation object.

Optionally, the control module 901 further includes:

a second control submodule, which is configured for:

determining whether there is a first temperature in the real-time acquired temperatures of the plurality of positions, wherein the first temperature is greater than a preset maximum temperature.

If there is a first temperature in the real-time acquired temperatures of the plurality of positions, determining whether the first perfusion channel is opened, wherein the first perfusion channel is configured to perfuse a first position with the liquid, and the first temperature is a temperature of the first position.

If the first perfusion channel is not opened, controlling the injection pump to open the first perfusion channel and returning to perform the step of determining whether there is a first temperature in the real-time acquired temperatures of the plurality of positions.

If the first perfusion channel has been opened, controlling the injection pump to increase a flow rate of the first perfusion channel according to a first preset increase and returning to perform the step of determining whether there is a first temperature in the real-time acquired temperatures of the plurality of positions, until the flow rate of the first perfusion channel reaches the preset maximum flow rate.

Optionally, the second control submodule is further configured to:

determining a ratio of the first temperature acquisition apparatus of the temperature acquisition apparatuses is greater than a first ratio after determining whether there is a first temperature in the temperatures of the plurality of positions and when the first temperature does not exist, wherein the temperature acquired by the first temperature acquisition apparatus within a preset temperature duration is less than a preset minimum temperature.

If the ratio is greater than the first ratio, controlling the injection pump to decrease a flow rate of a second perfusion channel according to a first preset decrease and returning to perform the step of determining whether the ratio of the first temperature acquisition apparatus of the temperature acquisition apparatuses is greater than the first ratio, until the flow rate of the second perfusion channel reaches a preset minimum flow rate, wherein the second perfusion channel is configured to perfuse a second position with the liquid, and the first temperature acquisition apparatus is configured to detect a temperature of the second position.

If the ratio is not greater than the first ratio, returning to perform the step of determining whether there is a first temperature in the real-time acquired temperatures of the plurality of positions.

Optionally, the apparatus further includes:

a setting module, which is configured to set respective preset maximum temperatures and respective preset minimum temperatures for the temperature acquisition apparatuses; and the second control submodule is further configured to determine the first perfusion channel and the second perfusion channel based on the respective preset maximum temperatures and the respective preset minimum temperatures.

Optionally, the control module 901 further includes:

a third control submodule, which is configured for:

determining whether a ratio of a second temperature in the real-time acquired temperatures of the plurality of positions is greater than a second ratio, wherein the second temperature is greater than a preset maximum temperature.

If the ratio of the second temperature is greater than the second ratio, determining a perfusion increment according to a preset increment rule;

determining an opening number according to the perfusion increment and the initial flow rate, and determining a third perfusion channel according to the opening number and a first determination rule; and controlling the injection pump to open the third perfusion channel and returning to perform the step of determining whether the ratio of the second temperature in the real-time acquired temperatures of the plurality of positions is greater than the second ratio, until all the perfusion channels are opened, wherein if the third perfusion channel has been opened, a perfusion channel adjacent to the third perfusion channel is opened.

Optionally, the third control submodule is further configured to control the injection pump to increase the flow rates of all the perfusion channels to the preset maximum flow rate after all perfusion channels are opened and the ratio of the second temperature is greater than the second ratio.

Optionally, the preset increment rule is: determining the perfusion increment according to a difference between the maximum temperature in the temperatures of the plurality of positions and the preset maximum temperature, wherein the difference between the maximum temperature and the preset maximum temperature is in direct proportional to the perfusion increment; and The first determination rule is: determining the third perfusion channel from near to far according to a distance from the second temperature acquisition apparatus and the opening number, wherein a temperature acquired by the second temperature acquisition apparatus is maximum.

Optionally, the third control submodule is further configured for:

determining whether a ratio of a third temperature acquisition apparatus in the temperature acquisition apparatuses is greater than a third ratio when the ratio of the second temperature is not greater than the second ratio, wherein a temperature acquired by the third acquisition apparatus is less than a preset minimum temperature.

If the ratio of the third temperature acquisition apparatus is greater than the third ratio, determining a perfusion decrement according to a preset decrement rule;

determining a closing number according to the perfusion decrement and the initial flow rate, and determining a fourth perfusion channel according to the closing number and a second determination rule; and controlling the injection pump to close the fourth perfusion channel and returning to perform the step of determining whether the ratio of the third temperature acquisition apparatus of the temperature acquisition apparatuses is greater than the third ratio, until all the perfusion channels are closed, wherein if the fourth perfusion channel has been closed, a perfusion channel adjacent to the fourth perfusion channel is closed.

If the ratio of the third temperature acquisition apparatus is not greater than the third ratio, returning to perform the step of determining whether the ratio of the second temperature in the real-time acquired temperatures of the plurality of positions is greater than the second ratio.

Optionally, the preset decrement rule is: determining the perfusion decrement according to a difference between the minimum temperature in the temperatures of the plurality of positions and the preset minimum temperature, wherein the difference between the minimum temperature and the preset minimum temperature is in direct proportional to the perfusion decrement; and The second determination rule is: determining the fourth perfusion channel from near to far according to a distance from the fourth temperature acquisition apparatus and the closing number, wherein a temperature acquired by the fourth temperature acquisition apparatus is minimum.

Optionally, the control module 901 further includes:

a fourth control submodule, which is configured to control a radio frequency ablation catheter to perform an ablation operation when the ablation task is triggered; and the fourth control submodule is further configured to control the injection pump to open all the perfusion channels to perfuse the ablation object with the liquid through the opened perfusion channels according to the initial flow rate after waiting for a preset duration.

Optionally, the fourth control submodule is further configured for:

determining a ratio of a third temperature in the real-time acquired temperatures of the plurality of positions is greater than a fourth ratio, wherein the third temperature is less than a preset minimum temperature.

If the ratio of the third temperature is greater than the fourth ratio, closing one opened perfusion channel randomly and returning to perform the step of determining whether the ratio of the third temperature in the real-time acquired temperatures of the plurality of positions is greater than the fourth ratio, until all the perfusion channels are closed.

If the ratio of the third temperature is not greater than the fourth ratio, determining whether a ratio of a fourth temperature in the real-time acquired temperatures of the plurality of positions is greater than a fifth ratio, wherein the fourth temperature is greater than a preset maximum temperature.

If the ratio of the fourth temperature is greater than the fifth ratio, determining whether there is an unopened perfusion channel.

If there is an unopened perfusion channel, opening one unopened perfusion channel randomly and returning to perform the step of determining whether the ratio of the fourth temperature in the real-time acquired temperatures of the plurality of positions is greater than the fifth ratio, until all the perfusion channels are opened.

If there is no unopened perfusion channel, increasing the flow rate of the perfusion channel according to a preset second increase and returning to perform the step of determining whether the ratio of the fourth temperature in the real-time acquired temperatures of the plurality of positions is greater than the fifth ratio, until the flow rate of the perfusion channel reaches the preset maximum flow rate.

If the ratio of the fourth temperature is not greater than the fifth ratio, returning to the step of determining whether the ratio of the third temperature in the real-time acquired temperatures of the plurality of positions is greater than the fourth ratio.

Specific processes for implementing respective functions of the above modules may refer to relevant contents of the embodiments as shown in FIG. 4 to FIG. 9, which will be omitted here.

In the embodiments of the present application, when the ablation task is triggered, the injection pump is controlled to open at least one perfusion channel through which the perfusion operation is executed according to the preset initial flow rate; and then, the injection pump is controlled to open or close some or all of the perfusion channels and/or adjust the flow rates of some or all of the perfusion channels according to the temperatures of the plurality of different positions of the ablation object, which are acquired by the plurality of temperature acquisition apparatuses in real time. Accordingly, the multi-path perfusion of the injection pump is adjusted intelligently and dynamically based on the real-time change in the temperatures of the plurality of different positions of the ablation object during the process of executing the ablation task. Since the perfusion volume of the injection pump is adjusted relatively purposefully and directionally along with the real-time change in the temperatures of the plurality of different positions of the ablation object, operation delays and operation errors caused by manual determination can be reduced. Meanwhile, the timeliness, the accuracy and the pertinence of liquid perfusion during the process of executing the ablation task can be improved. Accordingly, the injury of the ablation operation to the ablation object is reduced, and the safety of the radio frequency ablation operation is improved.

Figure 10:
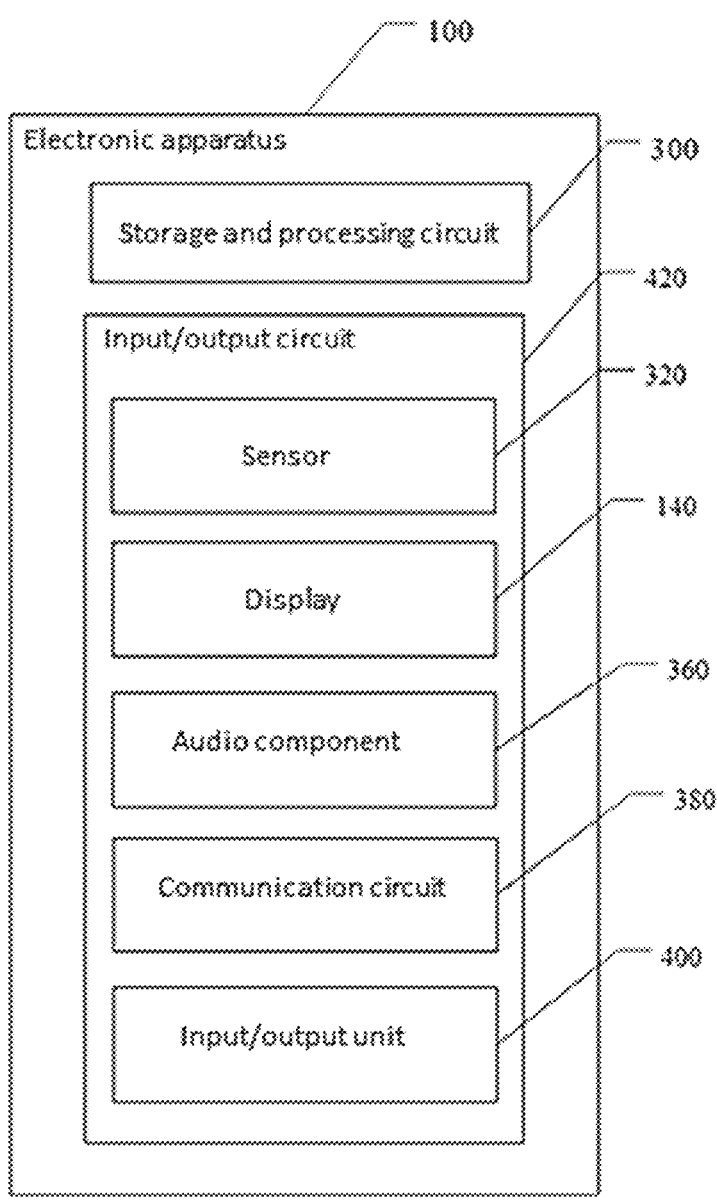
FIG. 10 is a schematic view of a hardware structure of an electronic apparatus provided by an embodiment of the present application.

Referring to FIG. 10, which is a schematic view of a hardware structure of an electronic apparatus provided by an embodiment of the present application.

Exemplarily, the electronic apparatus may be any one of various types of computer system devices that are non-removable or removable or portable and perform wireless or wired communication. Particularly, the electronic apparatus may be a desktop computer, a server, a mobile phone or a smart phone (for example, an iPhone-™-based phone, an Android-™-based phone), a portable game device (for example, Nintendo DS™, PlayStation Portable™, Gameboy Advance™, iPhone™), a laptop computer, a PDA, a portable Internet device, a music player and a data storage device, and other handheld devices. The electronic apparatus may further be other wearable devices (for example, such as electronic glasses, electronic clothes, electronic bracelets, electronic necklaces, smart watches or head-mounted devices (HMD)). In some instances, the electronic apparatus may perform multiple functions (for example, playing music, displaying video, storing pictures, and receiving and transmitting phone calls).

As shown in FIG. 10, the electronic apparatus 100 may include a control circuit, wherein the control circuit may include a storage and processing circuit 300. The storage and processing circuit 300 may include a memory, such as a hard disk drive memory, a non-transitory or non-volatile memory (such as a flash memory or other electronically programmable restricted deletion memory configured to form a solid-state drive), and a volatile memory (for example, a static or dynamic random access memory and the like), and the like, which are not limited in the embodiment of the present application. The processing circuit in the storage and processing circuit 300 may be configured to control the operation of the electronic apparatus 100. The processing circuit may be implemented based on one or more microprocessors, microcontrollers, digital signal processors, baseband processors, power management units, audio codec chips, application specific integrated circuits, display driver integrated circuits, and the like. The processor may be electrically coupled to the plurality of temperature acquisition apparatuses (such as minitype temperature sensors).

The storage and processing circuit 300 may be configured to execute software in the electronic apparatus 100, such as an Internet browsing application, a Voice over Internet Protocol (VOIP) telephone calling application, an email application, a media player application, an operating system function, and the like. The software may be configured to perform some control operations, for example, image capture based on a camera, ambient light measurement based on an ambient light sensor, proximity sensor measurement based on a proximity sensor, an information display function realized based on a status indicator such as a status indicator lamp of a LED, touch event detection based on a touch sensor, a function associated with displaying information on a plurality of (for example, layered) displays, an operation associated with performing a wireless communication function, an operation associated with acquiring and generating an audio signal, a control operation associated with acquiring and processing of button press event data, and other functions in the electronic apparatus 100, which are not limited in the embodiment of the present application.

Further, the memory stores an executable program code, and a processor coupled to the memory calls the executable program code stored in the memory to perform the multipath control method for injection pump described in the embodiments shown in FIG. 4 to FIG. 7 above.

The executable program code includes various modules in the multi-path control apparatus for injection pump described in the above embodiment shown in FIG. 9, for example, the control module 901 and the temperature acquisition module 902. Respective functions of the control module 901 and the temperature acquisition module 902 may particularly refer to relevant descriptions in the embodiment as shown in FIG. 9, which will be omitted here.

The electronic apparatus 100 may further include an input/output circuit 420. The input/output circuit 420 may be configured to enable the electronic apparatus 100 to input and output data, that is, to allow the electronic apparatus 100 to receive data from an external device and further allow the electronic apparatus 100 to output data from the electronic apparatus 100 to the external device. The input/output circuit 420 may further include a sensor 320. The sensor 320 may include an ambient light sensor, a proximity sensor based on light and capacitive, and a touch sensor (for example, a light-based touch sensor and/or a capacitive touch sensor, wherein the touch sensor may be a part of a touch display screen, or may be independently used as a touch sensor), an acceleration sensor, other sensors and the like.

The input/output circuit 420 may further include one or more displays, for example, a display 140. The display 140 may include one or a combination of more than one of a liquid crystal display, an organic light emitting diode display, an electronic ink display, a plasma display, and a display using other display technologies. The display 140 may include a touch sensor array (i.e., the display 140 may be a touch display screen). The touch sensor may be a capacitive touch sensor formed by an array of transparent touch sensor electrodes (for example, indium tin oxide (ITO) electrodes), or a touch sensor formed by using other touch technologies, such as sonic touch, pressure-sensitive touch, resistance touch and optical touch, which are not restricted by the embodiment of the present application.

The electronic apparatus 100 may further include an audio component 360. The audio component 360 may be configured to provide audio input and output functions for the electronic apparatus 100. The audio component 360 in the electronic apparatus 100 may include a speaker, a microphone, a buzzer, a tone generator, and other components for generating and detecting sounds.

The communication circuit 380 may be configured to provide the electronic apparatus 100 with the ability to communicate with an external device. The communication circuit 380 may include an analog and digital input/output interface circuit, and a wireless communication circuit based on a radio frequency signal and/or an optical signal. The wireless communication circuit in the communication circuit 380 may include a radio frequency transceiver circuit, a power amplifier circuit, a low noise amplifier, a switch, a filter and an antenna. For example, the wireless communication circuit in the communication circuit 380 may include a circuit for supporting near field communication (NFC) by transmitting and receiving a near-field coupled electromagnetic signal. For example, the communication circuit 380 may include a near-field communication antenna and a near-field communication transceiver. The communication circuit 380 may further include a cellular phone transceiver and an antenna, a wireless local area network transceiver circuit and an antenna, and the like.

The electronic apparatus 100 may further include a battery, a power management circuit and other input/output units 400. The input/output unit 400 may include a button, a joystick, a click wheel, a scroll wheel, a touch pad, a keypad, a keyboard, a camera, a light emitting diode, and other status indicators.

The user may input a command through the input/output circuit 420 to control the operation of the electronic apparatus 100, and may use the output data of the input/output circuit 420 to realize the reception of status information and other outputs from the electronic apparatus 100.

Further, embodiments of the present application further provide a computer-readable storage medium. The computer-readable storage medium may be provided in the electronic apparatus in each of the foregoing embodiments, and the computer-readable storage medium may be a memory in the storage and processing circuit 300 of the embodiment as shown in FIG. 10. A computer program is stored on the computer-readable storage medium, and is executed by the processor to realize the multi-path perfusion control method for injection pump according to the foregoing embodiments as shown in FIG. 4 to FIG. 7. Further, the computer-readable storage medium may further be a U disk, a mobile hard disk, a read-only memory (ROM), a RAM, a magnetic disk or an optical disk, and other various media that may store the program code.

In the several embodiments provided in the present application, it should be understood that the disclosed apparatus and method may be implemented in other ways. For example, the embodiments of the apparatus described above are merely illustrative. For example, the division of the modules is only a logical function division, or other divisions in practical implementations, for example, multiple modules or components may be combined or may be integrated into another system, or some features may be ignored or not performed. In addition, the displayed or discussed mutual coupling or direct coupling or communication connection may be indirect coupling or communication connection through some interfaces, apparatuses or modules, and may be in electrical, mechanical or other forms.

The modules described as separate components may or may not be physically separated, and the components displayed as modules may or may not be physical modules, that is, they may be located in one place, or they may be distributed onto a plurality of network modules. Some or all of the modules may be selected according to actual needs to achieve the objectives of the solutions of the embodiments.

In addition, the functional modules in the various embodiments of the present application may be integrated into one processing module, or each module may exist alone physically, or two or more modules may be integrated into one module. The above-mentioned integrated modules may be implemented in the form of hardware or a software functional module.

If the integrated module is implemented in the form of the software function module and sold or used as an independent product, it may be stored in a computer-readable storage medium. Based on such an understanding, the technical solution of the present application substantively, or a part thereof making a contribution to the prior art, or all or part of the technical solution may be embodied in the form of a software product stored in a readable storage medium, and the readable storage medium includes several instructions to enable a computer device (which may be a personal computer, a server, or a network device) to perform all or part of the steps of the methods according to the various embodiments of the present application. The above-mentioned readable storage medium includes a U disk, a mobile hard disk, a ROM, a RAM, a magnetic disk or an optical disk, and other media that may store the program code.

It should be noted that for simplicity of description, the foregoing method embodiments are all expressed as a series of action combinations, but because according to the present application, some steps may be performed in other sequences or simultaneously, those skilled in the art should appreciate that the present application is not limited by the described sequence of actions. Secondly, those skilled in the art should further appreciate that the embodiments described in the specification are all preferred embodiments, and the involved actions and modules are not necessarily all required by the present application.

In the above-mentioned embodiments, descriptions of the embodiments have particular emphasis respectively. For parts that are not described in detail in a certain embodiment, reference may be made to related descriptions of other embodiments.

The above is a description of the multi-path perfusion control method and apparatus for injection pump, the injection pump and the computer-readable storage medium according to the present application. For those skilled in the art, according to the ideas of the embodiments of the present application, changes may be made to specific implementations and application scopes. In summary, the content of this specification should not be construed as a limitation on the present application.

What is claimed is:

1. A multi-path perfusion control method for an injection pump, applied to a computer terminal, used for controlling the injection pump with a plurality of perfusion channels, the method comprising:
controlling the injection pump to open one perfusion channel randomly when an ablation task is triggered, so as to perfuse an ablation object with a liquid through the opened perfusion channel according to a preset initial flow rate; and
controlling a radio frequency ablation catheter to execute the ablation operation on the ablation object after the injection pump is controlled to open one perfusion channel randomly when the ablation task is triggered;
acquiring temperatures of a plurality of positions of the ablation object in real time by a plurality of temperature acquisition apparatuses; and
controlling the injection pump to open or close some or all of the perfusion channels and/or controlling the injection pump to adjust flow rates of some or all of the perfusion channels according to a real-time change in the temperatures of the plurality of positions.

2. The method according to claim 1, wherein controlling the injection pump to open or close some or all of the perfusion channels and/or controlling the injection pump to adjust the flow rates of some or all of the perfusion channels according to the real-time change in the temperatures of the plurality of positions comprises:
determining whether there is a first temperature in the real-time acquired temperatures of the plurality of positions, wherein the first temperature is greater than a preset maximum temperature:
when there is a first temperature, determining whether the first perfusion channel is opened, wherein the first perfusion channel is configured to perfuse a first position with a liquid, and the first temperature is a temperature of the first position:
when the first perfusion channel is not opened, controlling the injection pump to open the first perfusion channel and returning to execute the step of determining whether there is a first temperature in the real-time acquired temperatures of the plurality of positions; and
when the first perfusion channel has been opened, controlling the injection pump to increase a flow rate of the first perfusion channel according to a first preset increase and returning to execute the step of determining whether there is a first temperature in the real-time acquired temperatures of the plurality of positions, until the flow rate of the first perfusion channel reaches the preset maximum flow rate.

3. The method according to claim 1, wherein
after controlling the radio frequency ablation catheter to execute the ablation operation on the ablation object after the injection pump is controlled to open one perfusion channel randomly when the ablation task is triggered, further comprises:
controlling the injection pump to open all the perfusion channels after waiting for a preset duration, so as to perfuse the ablation object with the liquid through the opened perfusion channel according to the initial flow rate.

4. A multi-path perfusion control apparatus for an injection pump, wherein the apparatus is configured for controlling the injection pump with a plurality of perfusion channels, and comprises:
a control module configured for controlling the injection pump to open one perfusion channel randomly when an ablation task is triggered, so as to perfuse an ablation object with a liquid through the opened perfusion channel according to a preset initial flow rate and controlling a radio frequency ablation catheter to execute the ablation operation on the ablation object after the injection pump is controlled to open one perfusion channel randomly when the ablation task is triggered; and a temperature acquisition module configured for acquiring temperatures of a plurality of positions of an ablation object in real time by a plurality of temperature acquisition apparatuses;

the control module further configured for controlling the injection pump to open or close some or all of the perfusion channels and/or controlling the injection pump to adjust flow rates of some or all of the perfusion channels according to a real-time change in the temperatures of the plurality of positions.

5. An electronic apparatus, comprising:

a non-transitory memory and a processor, the non-transitory memory storing an executable program code;

the processor being electrically coupled to the non-transitory memory and a plurality of temperature acquisition apparatuses; and the processor calling the executable program code stored in the non-transitory memory to execute the multi-path perfusion control method for injection pump according to claim 1.

6. An injection pump, comprising a controller, a plurality of temperature acquisition apparatuses and a multi-path injection structure, the injection structure comprising a syringe, an extension tube, a push rod and a driving device, one end of the extension tube being connected to the syringe and the other end being provided with at least one of the temperature acquisition apparatus, and each path of the injection structure forming a perfusion channel; and the controller being electrically coupled to the plurality of temperature acquisition apparatuses and electrically connected to the multi-path injection structure, for executing steps of the multi-path perfusion control method for injection pump according to claim 1.

7. A non-transitory computer-readable storage medium on which a computer program is stored, wherein the computer program, when executed by a processor, implements the multi-path perfusion control method for injection pump according to claim 1.

* * * * *